(12) United States Patent
Creighton, IV et al.

(10) Patent No.: US 7,019,610 B2
(45) Date of Patent: Mar. 28, 2006

(54) MAGNETIC NAVIGATION SYSTEM

(75) Inventors: Francis M. Creighton, IV, St. Louis, MO (US); Seth Burgett, Glen Carbon, IL (US)

(73) Assignee: Stereotaxis, Inc., St. Louis, MO (US)

( * ) Notice: Subject to any disclaimer, the term of this patent is extended or adjusted under 35 U.S.C. 154(b) by 407 days.

(21) Appl. No.: 10/347,525

(22) Filed: Jan. 17, 2003

(65) Prior Publication Data

US 2004/0030324 A1   Feb. 12, 2004

Related U.S. Application Data

(63) Continuation-in-part of application No. 10/056,227, filed on Jan. 23, 2002.

(51) Int. Cl.
   *H01F 7/02* (2006.01)
(52) U.S. Cl. .................. 335/306; 600/9; 600/114; 128/899
(58) Field of Classification Search ............... 335/216, 335/296–306; 324/318–320; 600/410, 9–14, 600/114, 424; 128/899
   See application file for complete search history.

(56) References Cited

U.S. PATENT DOCUMENTS

| | | | | |
|---|---|---|---|---|
| 5,735,278 A | * | 4/1998 | Hoult et al. | 600/422 |
| 5,900,793 A | * | 5/1999 | Katznelson et al. | 335/296 |
| 6,029,081 A | * | 2/2000 | DeMeester et al. | 600/410 |
| 6,128,522 A | * | 10/2000 | Acker et al. | 600/411 |
| 6,317,618 B1 | * | 11/2001 | Livni et al. | 600/410 |

* cited by examiner

*Primary Examiner*—Ramon M. Barrera
(74) *Attorney, Agent, or Firm*—Harness Dickey & Pierce PLC

(57) ABSTRACT

A system for magnetically navigating a medical device in an operating region within the body of a patient. The system includes a magnet having a front field projecting from the front of the magnet sufficient to project a magnetic field into the operating region in the patient. The magnet is mounted for movement between a navigation position in which the magnet is located adjacent to the patient with the front of the magnetic generally facing the operating region, and an imaging position in which the magnet is spaced from the patient and the front generally faces away from the operating region.

3 Claims, 34 Drawing Sheets

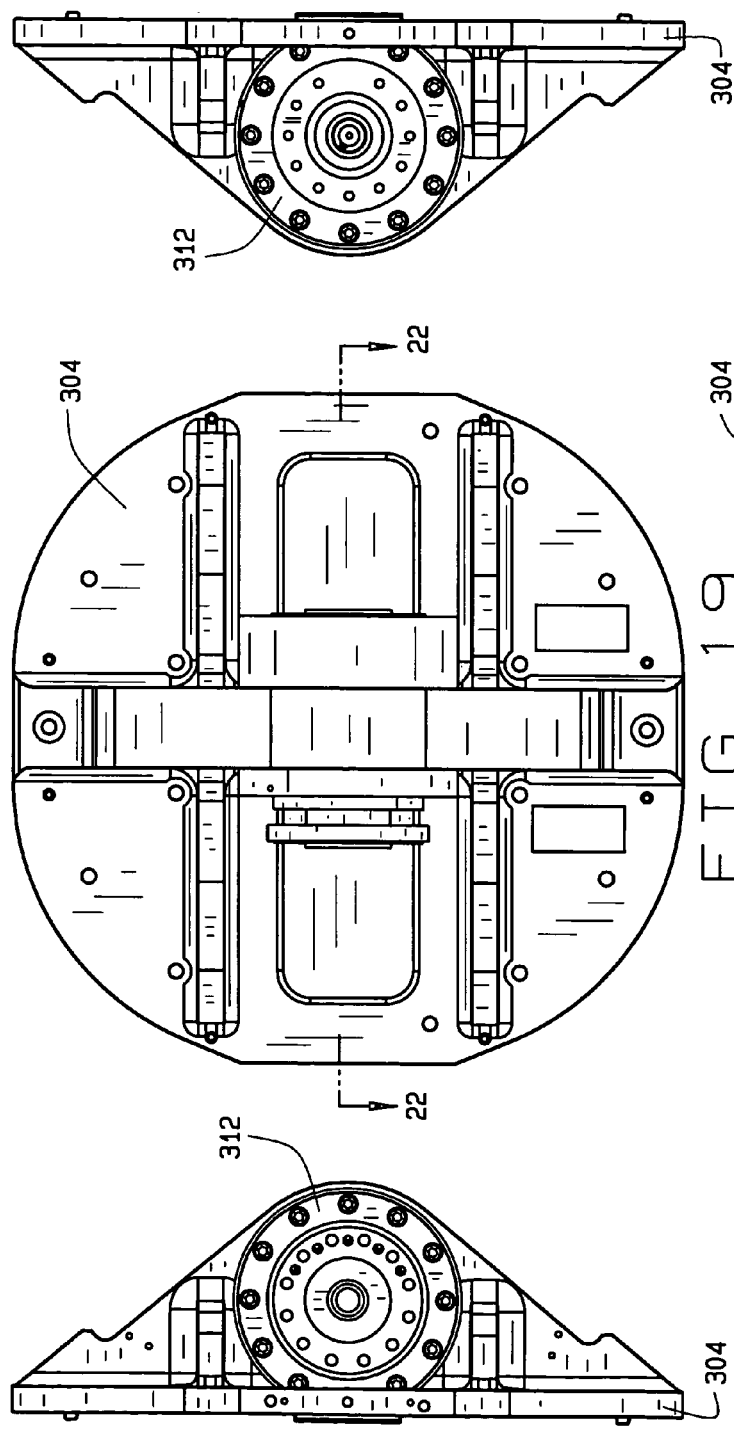

MAGNETIC NAVIGATION SYSTEM

CROSS REFERENCE TO RELATED APPLICATION

This is a Continuation-in-Part of U.S. patent application Ser. No. 10/056,227, filed Jan. 23, 2002, for Rotating and Pivoting Magnet for Magnetic Navigation, incorporated herein by reference.

BACKGROUND OF THE INVENTION

This system relates to magnetic navigation of medical devices in the body, and in particular to a system for applying a magnetic field of selected direction to an operating region in a subject's body to orient a magnetically responsive medical device.

Magnetic navigation of medical devices has significantly improved to ability of medical professionals to control medical devices in the body. Early magnetic navigation techniques involved the use of superconducting magnets. While these techniques were, and remain, highly effective, advances in permanent magnetic materials and in the design of permanent magnets, have made it possible to use permanent magnets for magnetic navigation. While the magnetic fields created by superconducting magnets can be readily changing the currents in the superconducting electromagnetic coils, in order to change the magnetic field created by permanent magnets for navigation, it is generally necessary to change the position and/or orientation of the permanent. In order to accurately control the magnetic field applied by permanent magnets, it is necessary to accurately control the position and/or orientation of the permanent magnet.

SUMMARY OF THE INVENTION

The present invention relates to a magnetic navigation system, and in particular to a system including magnet units comprising a permanent magnet, and a support for controlling the position and orientation of a permanent magnet. The system is adapted for magnetically navigating a medical device in an operating region within the body of a patient. Generally, the system comprises a magnet having a front field projecting from the front of the magnet sufficient to project a magnetic field into the operating region in the patient. The magnet is mounted for movement between a navigation position in which the magnet is located adjacent to the patient with the front of the magnetic generally facing the operating region, and an imaging position in which the magnet is spaced from the patient and the front generally faces away from the operating region.

According to another aspect of the invention the system includes a magnet system comprising: a magnet and a support for mounting the magnet and changing the position and orientation of the magnet to change the direction of magnetic field applied to the operating region. The support is preferably capable of pivoting the magnet about a first axis that rotates about a second axis perpendicular to the first axis, and translating the magnet, preferably parallel to the second axis.

BRIEF DESCRIPTION OF THE DRAWINGS

FIG. 19 is a front elevation view of the front plate of the phi drive mechanism;

FIG. 20 is a left side elevation view of the front plate of the phi drive mechanism;

FIG. 21 is a right side elevation view of the front plate of the phi drive mechanism;

FIG. 22 is a horizontal transverse view of the front plate of the phi drive mechanism, taken along the plane of line 22—22 in FIG. 19;

FIG. 33 is an a top plan view of the z drive mechanism

Corresponding reference numerals indicate corresponding parts throughout the several views of the drawings.

DETAILED DESCRIPTION OF THE INVENTION

Figure 1:
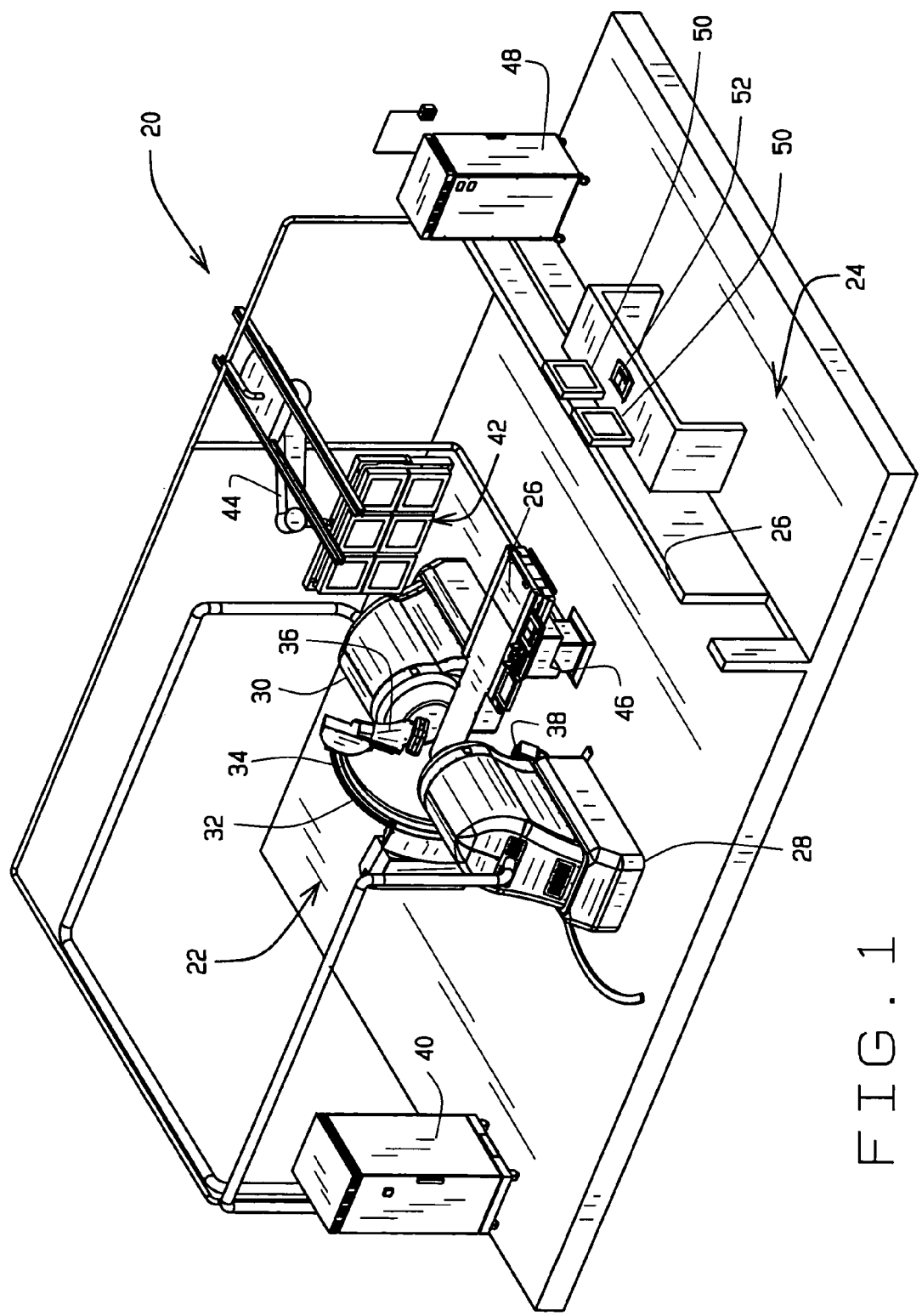
FIG. 1 is a perspective view of a magnetic surgery suite incorporating magnet assemblies in accordance with the principles of this invention.
Figure 1A:
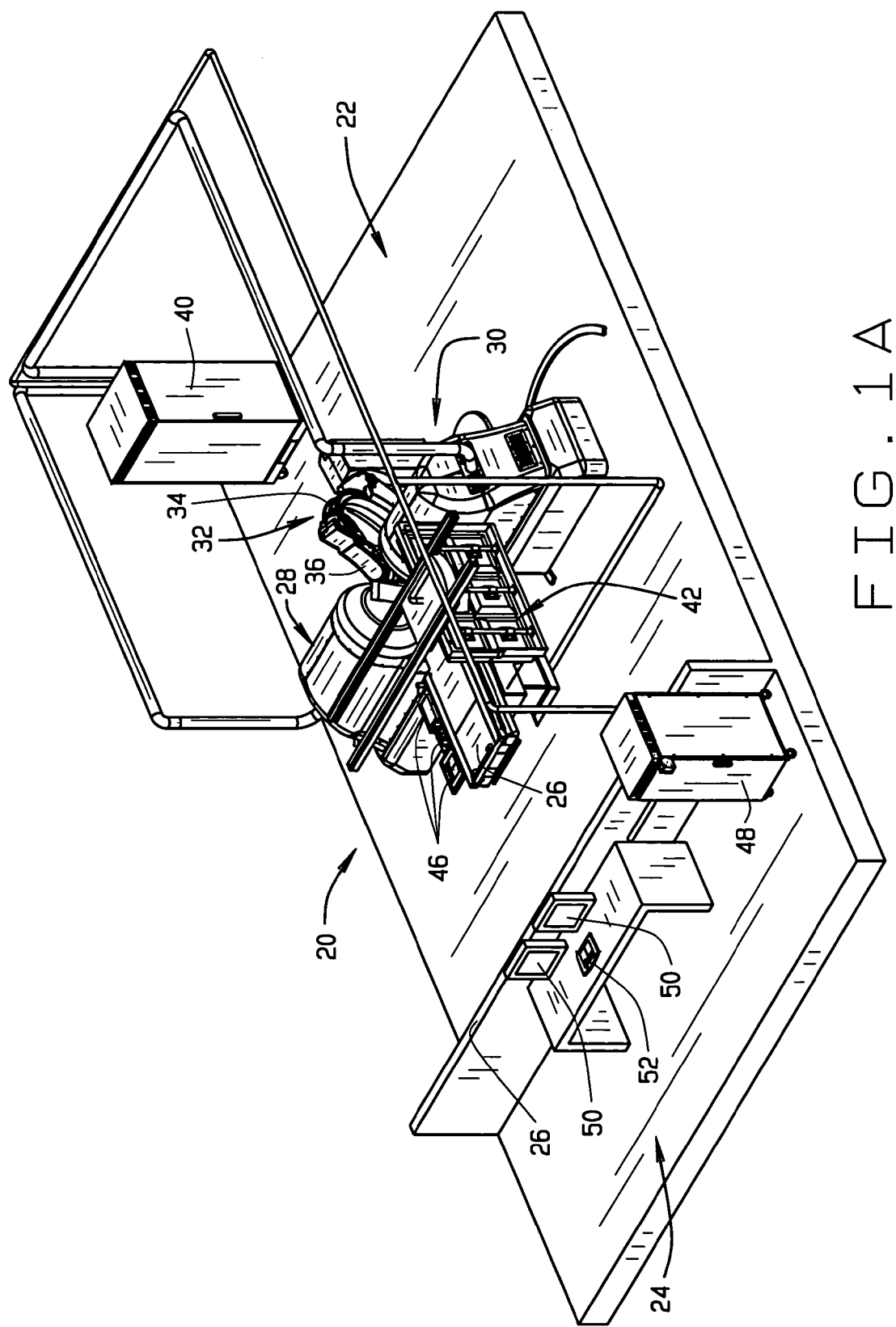
FIG. 1A is a top plan view of the magnetic surgery suite.

A magnetic surgery suite incorporating magnet units in accordance with the principles of this invention is indicated generally as 20 in FIG. 1. As shown in FIG. 1, the suite 20 comprises an operating room 22 and a control room 24. The control room 24 is preferably adjacent to the operating room 22, and has a window 26 from which the procedure taking place in the operating room 22 can be viewed. However, the control room 24 does not have to be adjacent to the operating room 22, and instead could be located remotely from the operating room, for example on a different floor, or in a different building, or even in a different city.

The operating room 22 includes a patient support, such as a patient bed 26, and a pair of magnet units 28 and 30, disposed on opposite sides of the patient bed to project a magnetic field into the operating region in a patient on the patient bed. The operating room also includes an imaging system 32, comprising a C-arm mounting at least one x-ray source 34 and at least one x-ray receiver 36, such as an amorphous silicon imaging plate. Cabinets 38 and 40 are provided for computer controllers and other electronics for operating the magnet units 28 and 30 and the imaging system 32. A plurality of displays 42 (six in this preferred embodiment) are mounted on an articulating arm 44 from the ceiling. The displays 42 display images from the imaging system 32, and screens from the control system for operating the magnet units 28 and 30. A plurality of controls 46 are provided on the patient bed 26 for operating a user interface to control the magnet units 28 and 30, in conjunction with the screens displayed on the displays 42.

The control room 24 includes a cabinet 48 for a processor for operating the user interface for controlling the magnet units 28 and 30. A plurality of displays 50 (two in this preferred embodiment) are provided for displaying images from the imaging system 32, and screens from the user interface. A plurality of controls 52 are provided on the patient bed 26 for operating a user interface to control the magnet units 28 and 30, in conjunction with the screens on the displays 52.

Each of the magnet units 28 and 30 projects a strong magnet field from its front face, so that together, the magnets provide a magnet field of sufficient strength to orient a magnetic medical device in an operating region in the patient on the patient bed 26. Because of the strength of the field projected by the magnet units 28 and 30, the units are preferably rotatably mounted to swing between an operative position in which the units face the patient support, and project a field into the operating region in the patient on the patient bed, and a stowed position, in which the magnet units do not face the patient bed.

Figure 2:
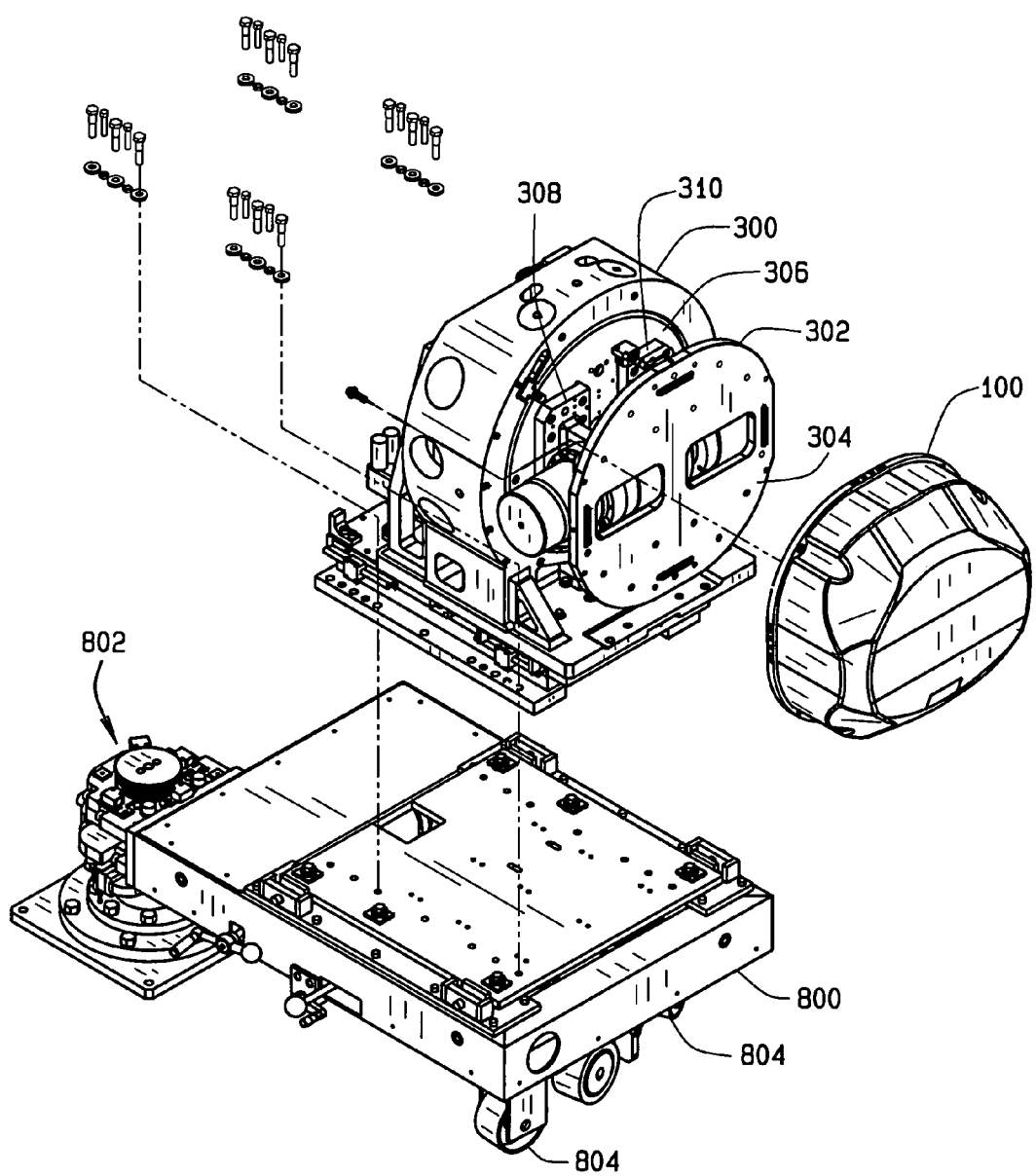
FIG. 2 is an exploded front perspective view of one of the magnet assemblies (the other magnet assembly being a mirror image thereof), with the cover removed to show details of construction.

As shown in FIG. 2, each of the magnet units 28 and 30 comprises a magnet 100, a mechanism 200 for moving the magnet to change the magnetic field applied by the magnet 100 to the operating region in a patient, and a pedestal 700, for supporting the mechanism 200 and magnet 100. As described in more detail below the magnet 100 is preferably a compound magnet designed so that relatively small translations and/or rotations result in significant changes in the magnetic field direction projected into an operating region in the patient. As described in more detail below, the mechanism 200 is adapted to support and translate and/or rotate the magnet 100 to change the direction of the field applied by the magnet to the operating region in the patient. The magnet 100 and the mechanism 300 are preferably designed so that they can project a magnetic field in any direction in the operating region in the patient, or at least so that when both magnet units 28 and 30 are positioned on opposite sides of the patient, the combined effect of the magnets from the units projects a magnetic field in any direction.

In this preferred embodiment, the mechanism preferably provides three movements of the magnet 100: translation of the magnet toward and away from the patient (referred to herein as translation in the z-direction), rotation of the magnet about an axis parallel to the z-direction, referred to herein as rotation in the θ-direction, and pivoting of the magnet about an axis perpendicular to the θ-axis, referred to herein as pivoting in the φ direction. The movements of the magnet 100 in the z direction, the θ-direction, and the φ direction permitted by the mechanism 300 are sufficient to create a magnetic field of suitable strength for magnetic navigation, in any direction in the operating region in the patient. Of course, additional or different translations and or rotations could be provided for the same or different magnet design. The strength of the field projected by the magnets is preferably at least 0.05, and more preferably at least 0.09.

The magnet 100 is preferably comprised of a plurality of block 102 arranged and mounted on a backing plate 104, for example with adhesive the magnet 100 further includes a cover 106, preferably with a smooth, contoured finished surface enclosing the assembly of blocks 102. Each of the blocks is made of a permeable magnetic material, and has a size, shape, position and magnetization direction to optimize field properties (direction and strength) while accommodating manufacturing. Examples of suitable magnets are disclosed in magnets such as those disclosed in U.S. patent application Ser. No. 10/082,715, filed Feb. 25, 2002, U.S. patent application Ser. No. 10/056,227, filed Jan. 23, 2003, and/or U.S. patent application Ser. No. 09/546,840, filed Apr. 11, 2000, the disclosures of all of which are incorporated herein by reference.

The magnet 100 and mechanism 300 are mounted on pedestal 800. As indicated above, and described in more detail below, the pedestal 800 is mounted for pivoting about a post 802, and has wheels 804 which allow the pedestal to pivot from a stowed position, in which the magnet 100 generally faces away from the patient, to an operative position in which the magnet generally faces the patient.

Figure 3:
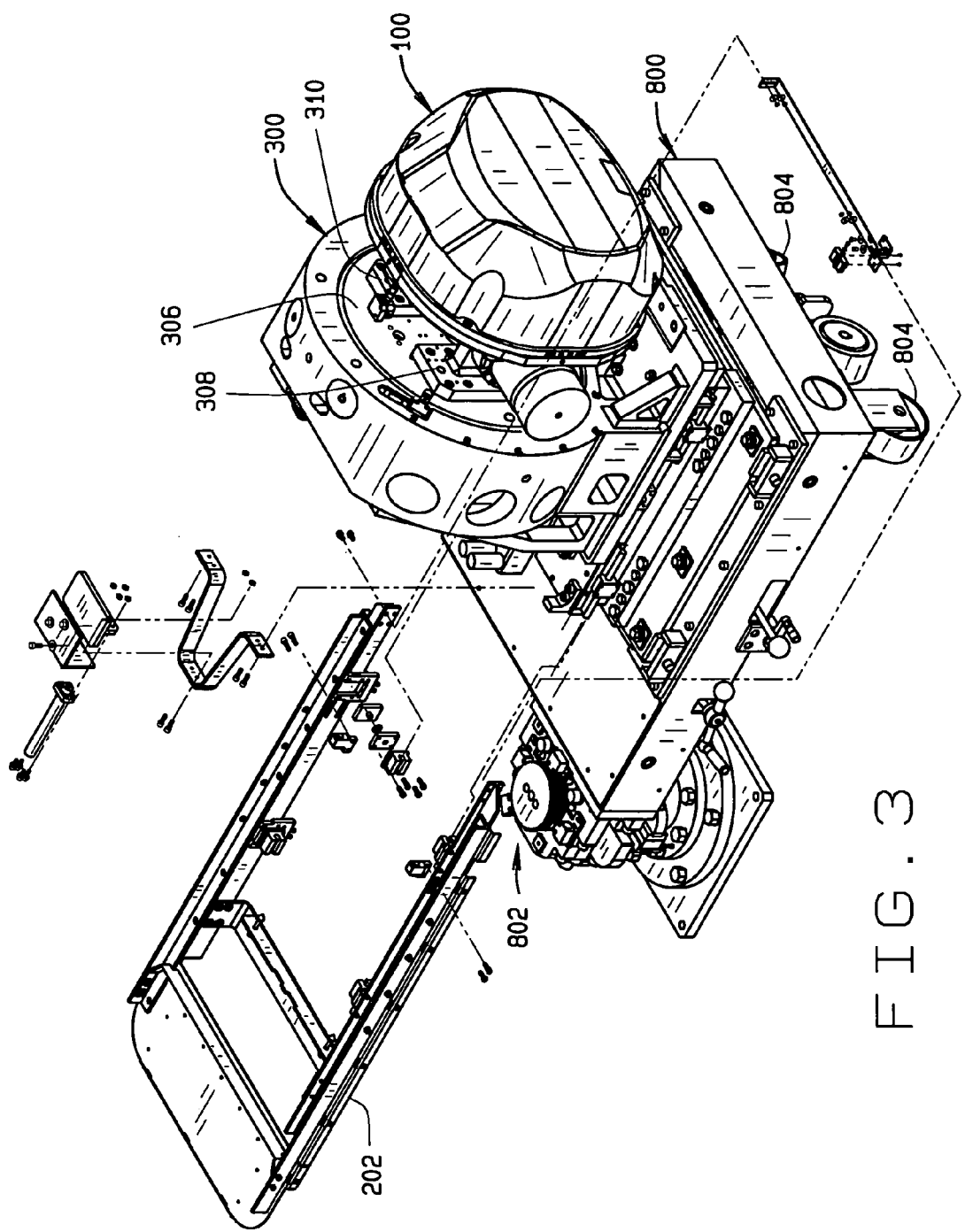
FIG. 3 is a front perspective view of the magnet assembly, with the cover removed.
Figure 4:
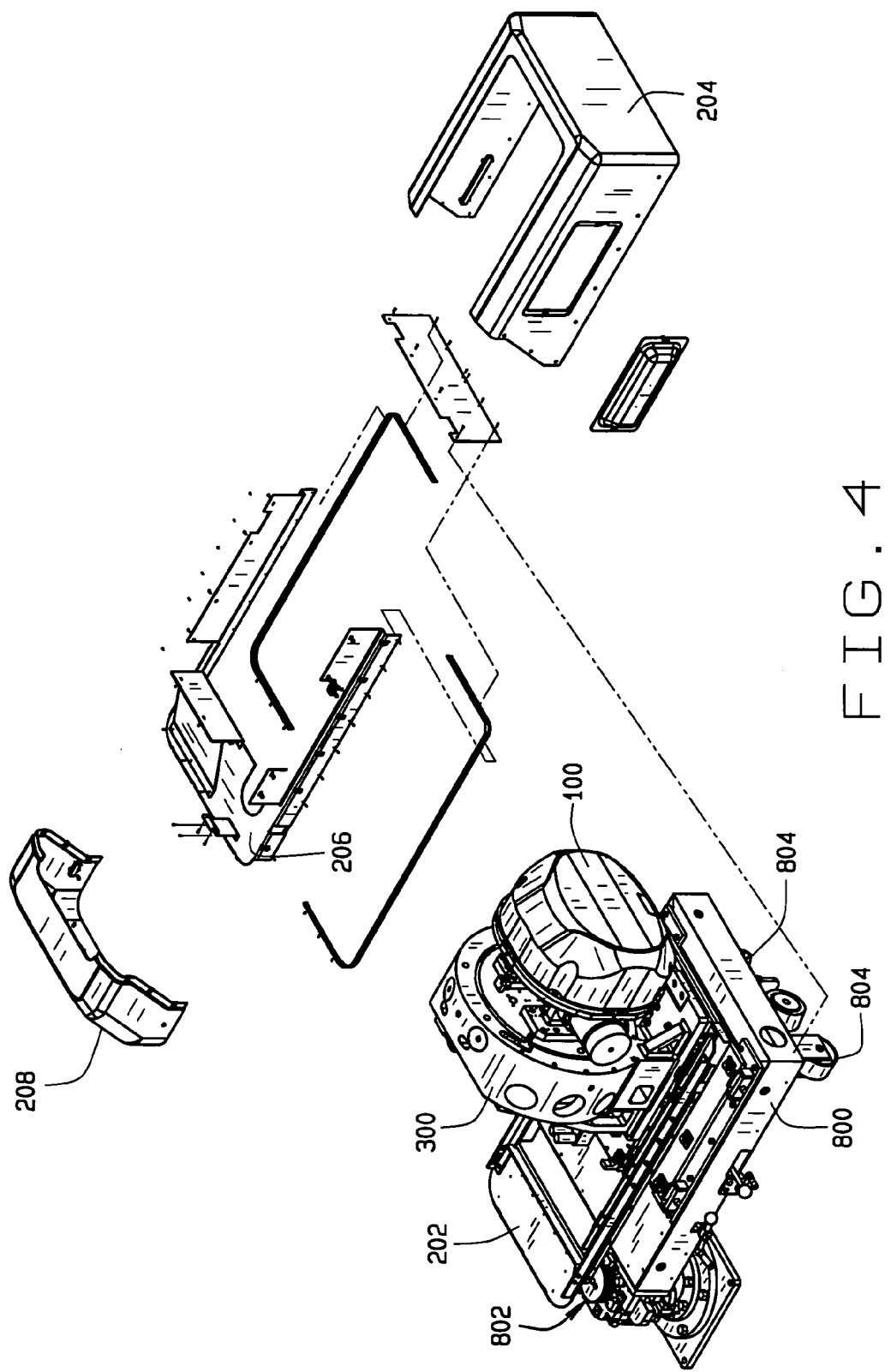
FIG. 4 is a front perspective view of the magnet assembly, showing the lower cover.
Figure 5:
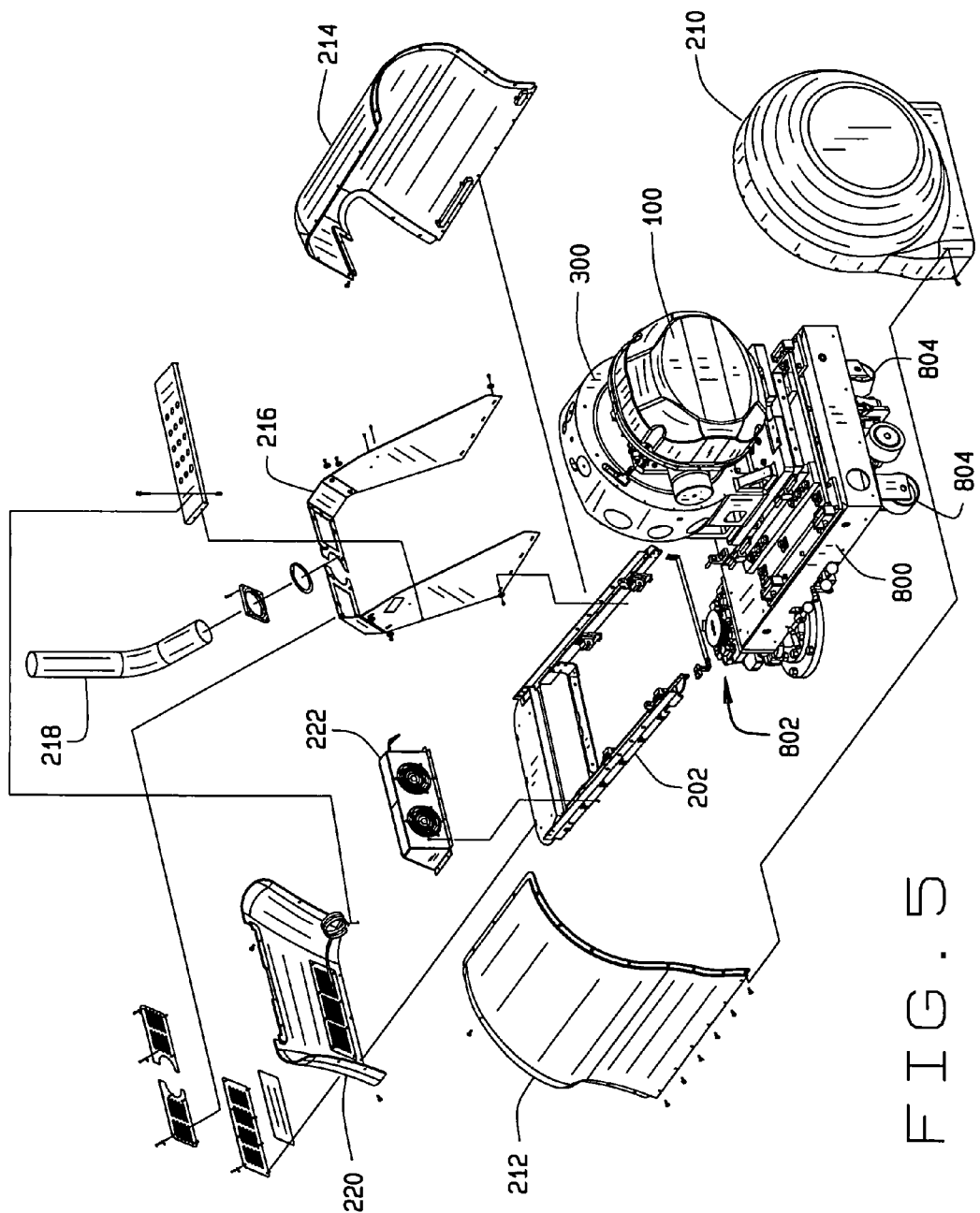
FIG. 5 is a front perspective view of the magnet assembly, showing the upper cover.
Figure 6:
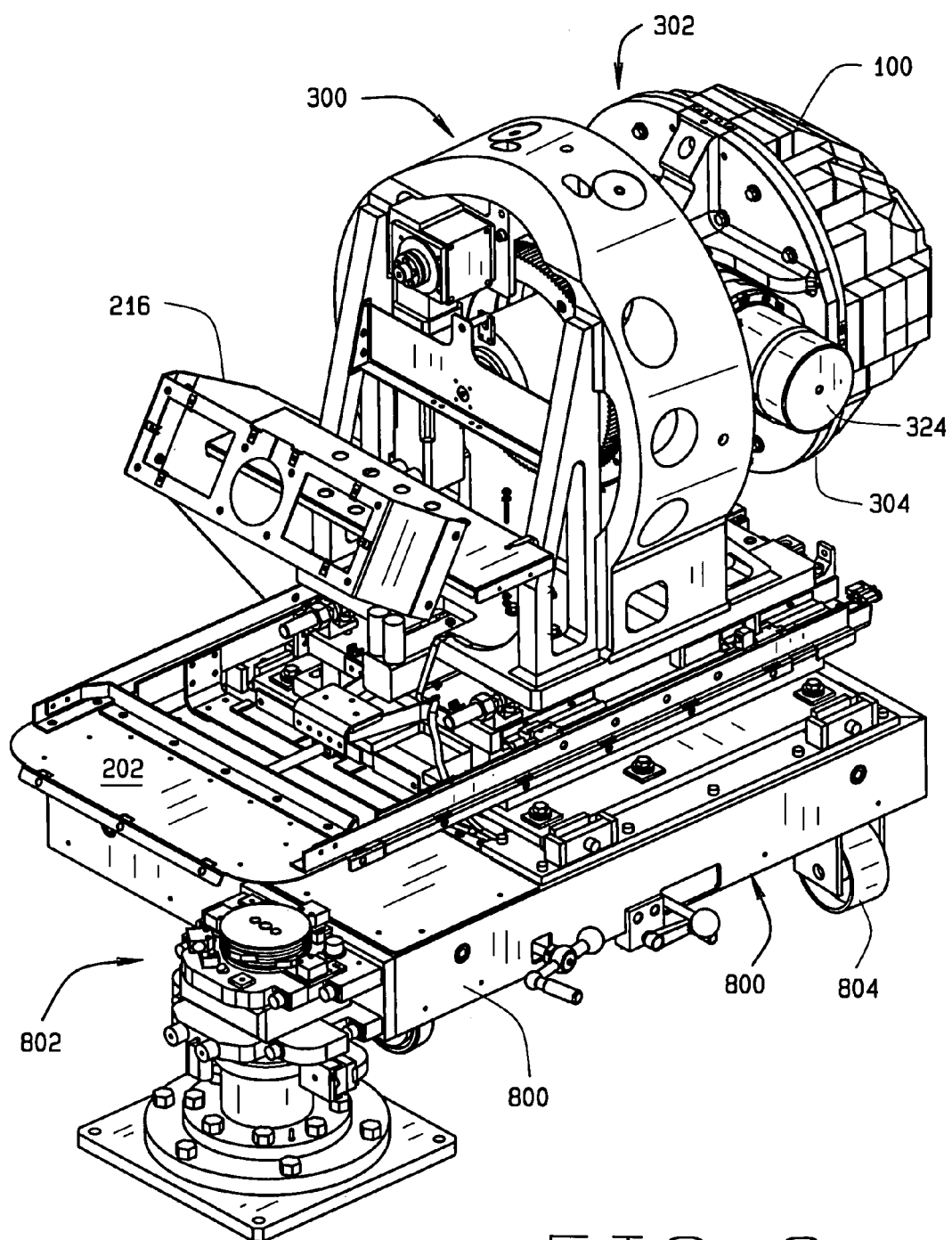
FIG. 6 is a rear perspective view of the magnet assembly.
Figure 7:
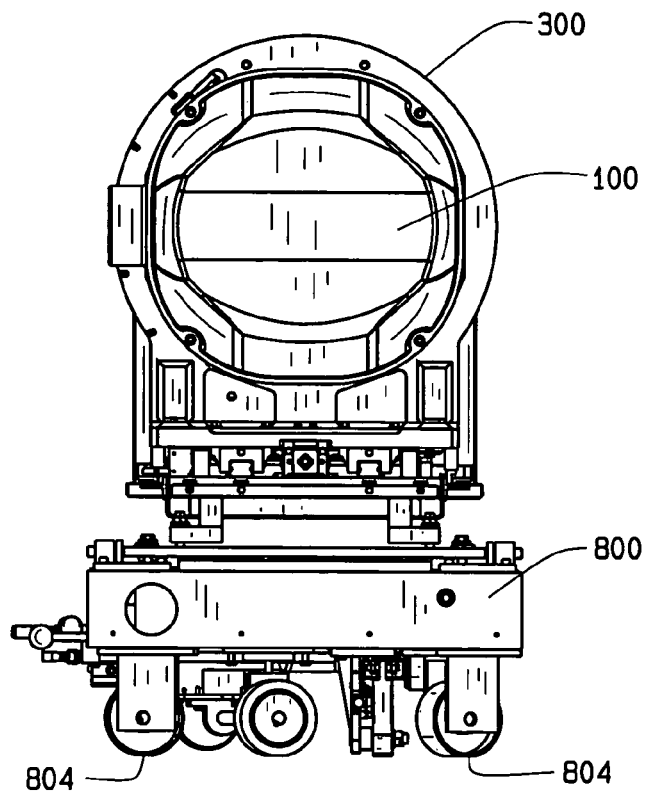
FIG. 7 is a front elevation view of the magnet assembly.
Figure 9:
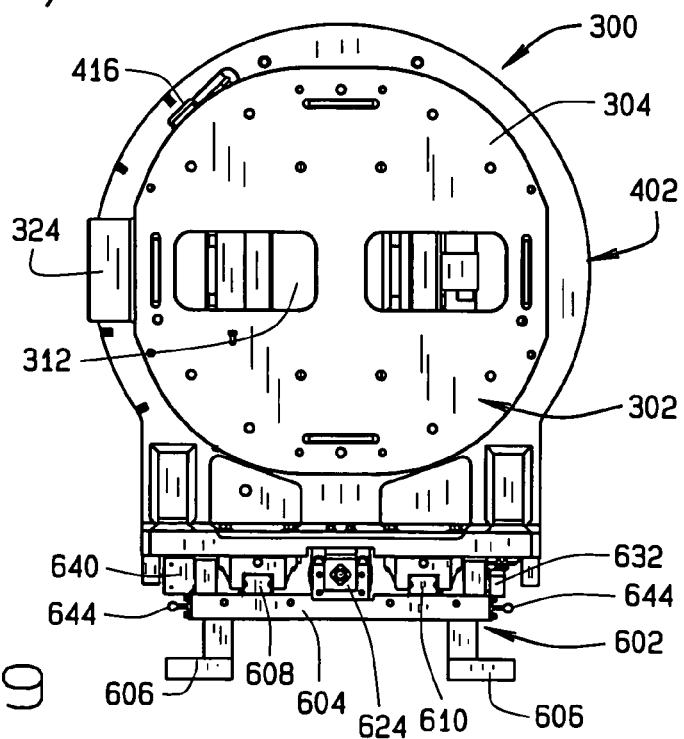
FIG. 9 is a front elevation view of the positioner system of the magnet assembly.

The magnet 100 and mechanism 300 are preferably enclosed is a cover 200 to protect the mechanism from interference, to prevent persons from being injured or property from being damaged by the mechanism, to reduce patient anxiety, and to enhance the appearance of the unit. As shown in FIG. 3, this cover includes a frame 202 slidably mounted around the base of the mechanism 300. As shown in FIG. 4, the cover also comprises a front base cap 204, which is generally U-shaped and adapted to be secured on the front and sides of the pedestal 800, a top base cap 206, which is adapted to be secured over the top of the pedestal, around the mechanism 300, and a rear base cap 208, which is adapted to be secured on the back of the pedestal cap device. As shown in FIG. 5, the cover 200 also comprises a front panel 210, adapted for mounting on the frame 202 over the front of the magnet 100 and mechanism 300, and left and right side panels 212 and 214 adapted for mounting on the frame 202 over the sides of the magnet and mechanism. An inverted U-shaped frame 216 is mounted on the frame 202 over the back of the mechanism 300. The frame 216 mounts a conduit 218 for enclosing power and control leads, and a back panel 220 for covering the back of the mechanism. A cooling fan unit 222 is mounted on the frame 202, inside the panel 220 to circulate air inside the cover through louvered openings formed in the cover 220.

Figure 8:
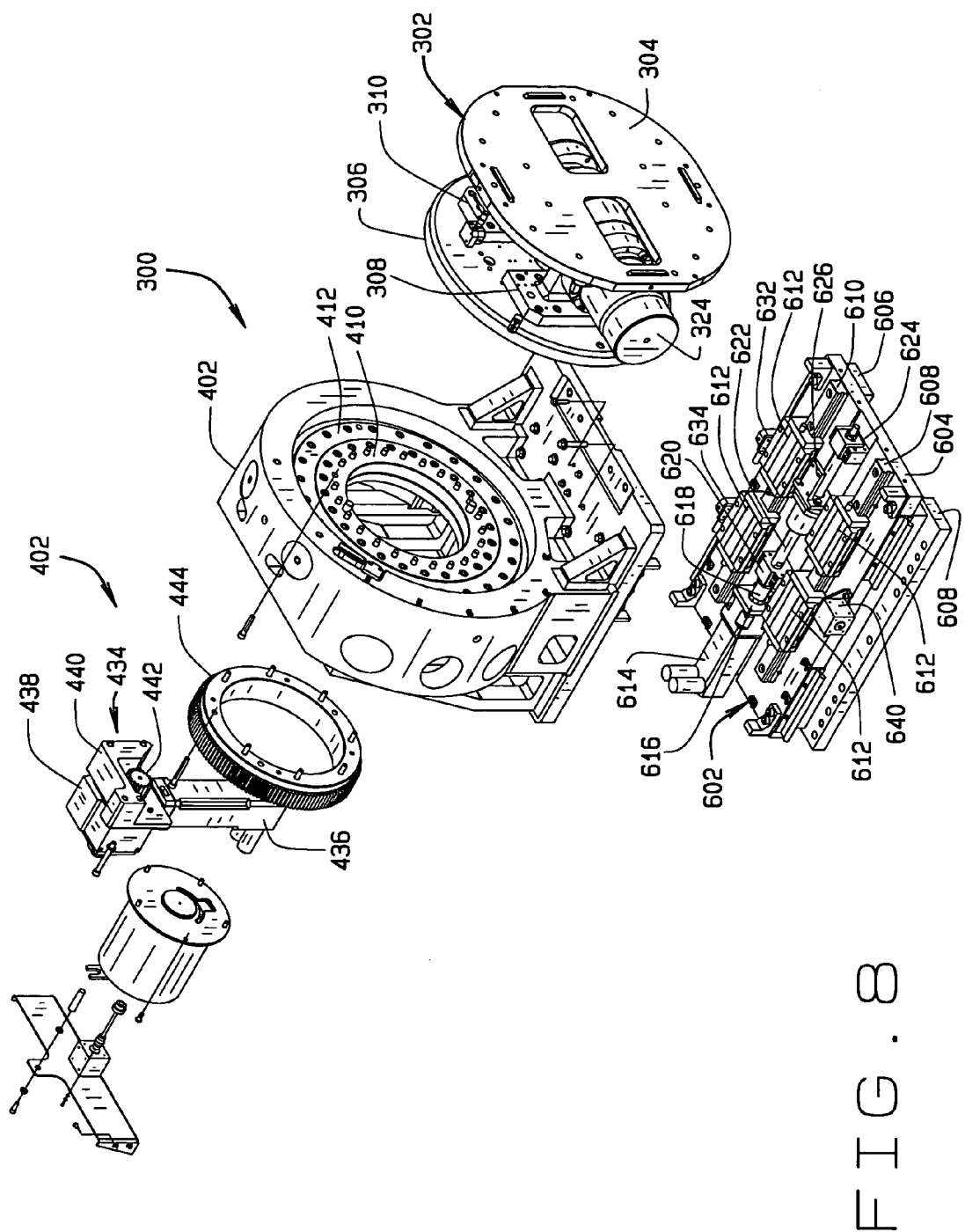
FIG. 8 is a further exploded front perspective view of the positioner system of the magnet assembly
Figure 10:
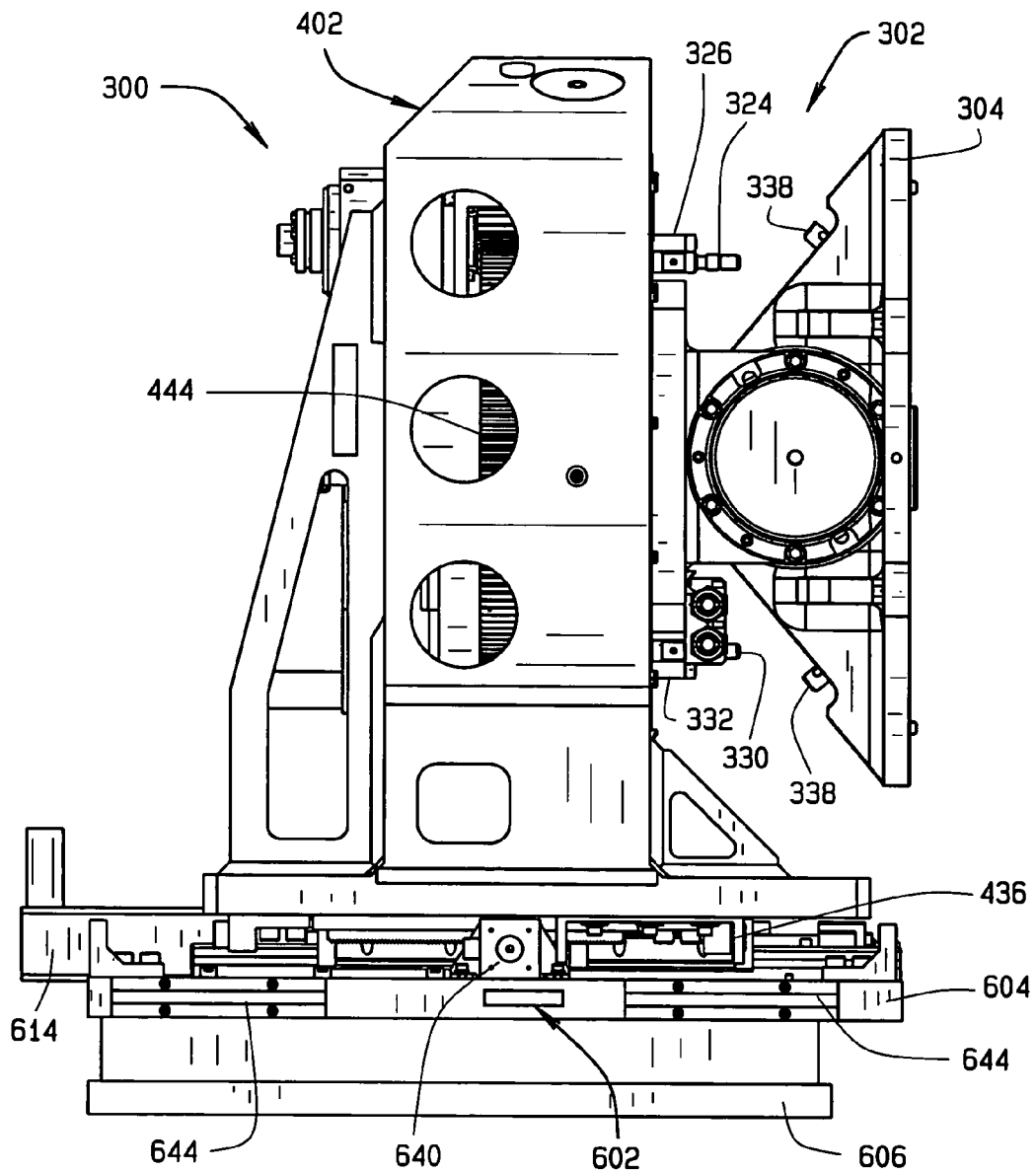
FIG. 10 is a left side elevation view of the positioner system of the magnet assembly
Figure 11:
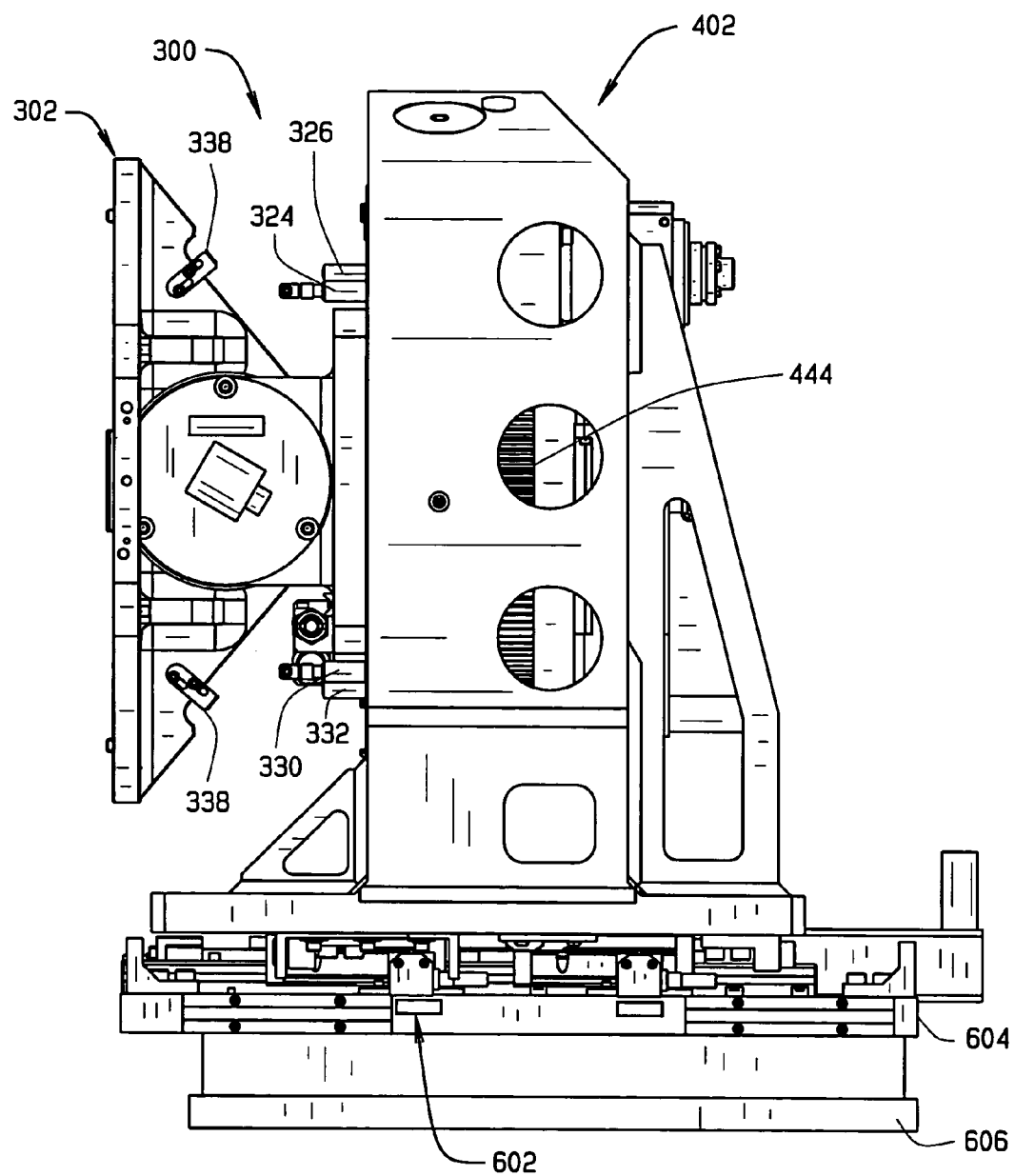
FIG. 11 is a right side elevation view of the positioner system of the magnet assembly.
Figure 12:
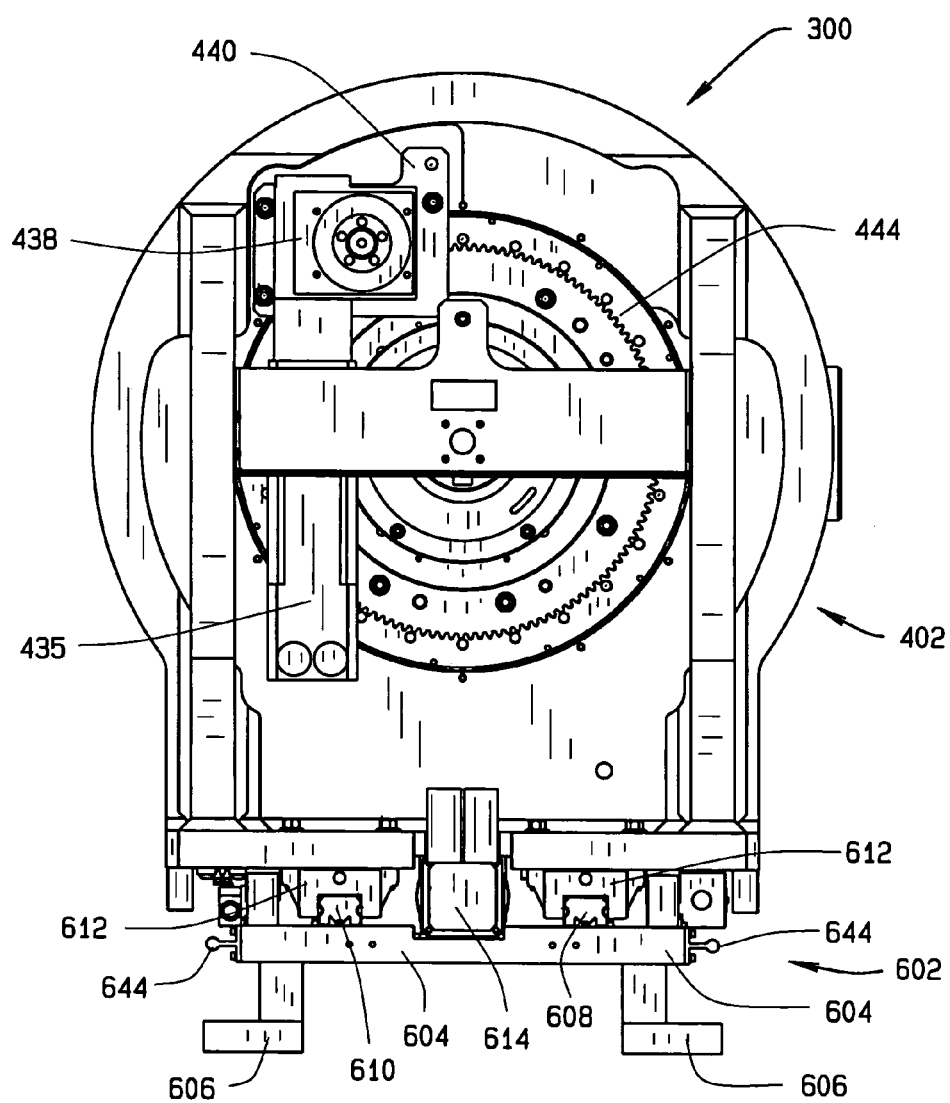
FIG. 12 is a rear elevation view of the positioner system.
Figure 13:
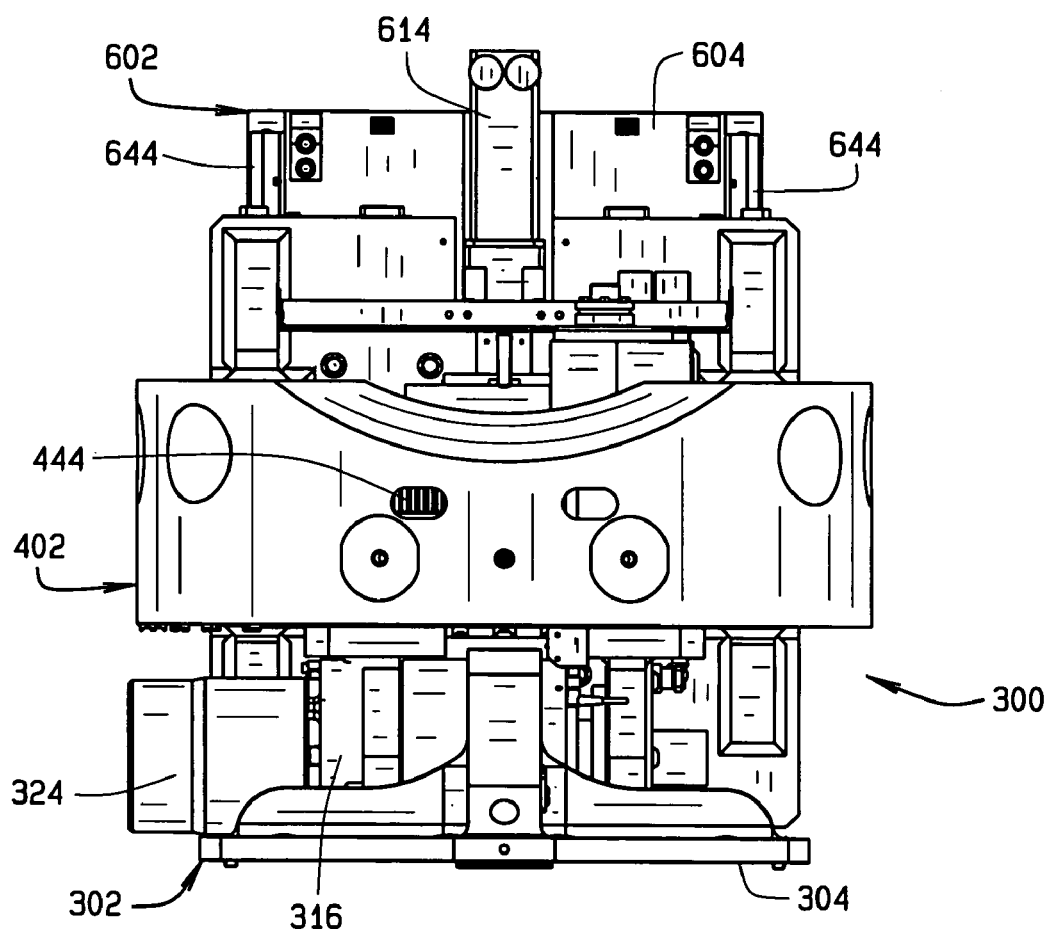
FIG. 13 is a top plan view of the positioner system.
Figure 14:
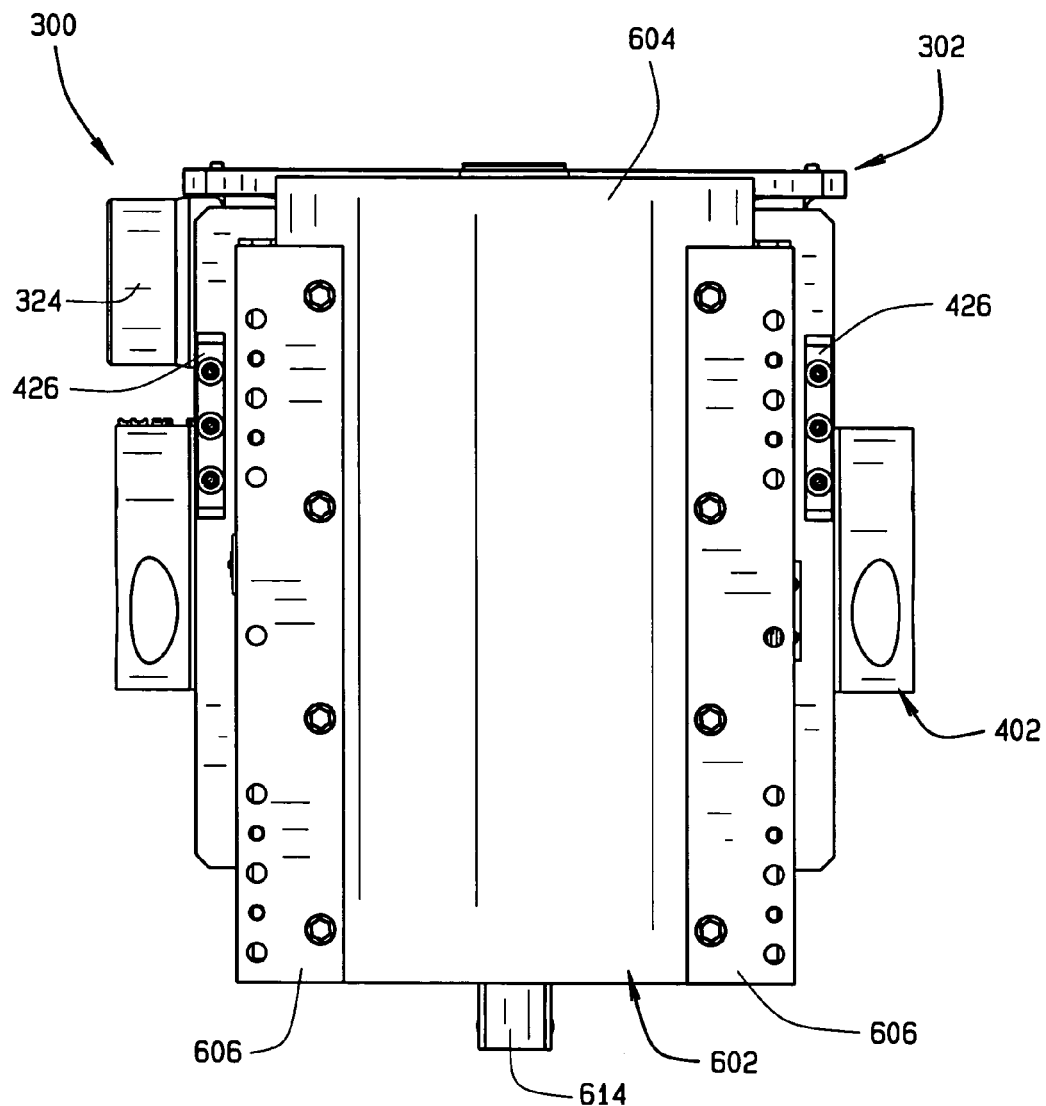
FIG. 14 is a bottom plan view of the positioner system.
Figure 15:
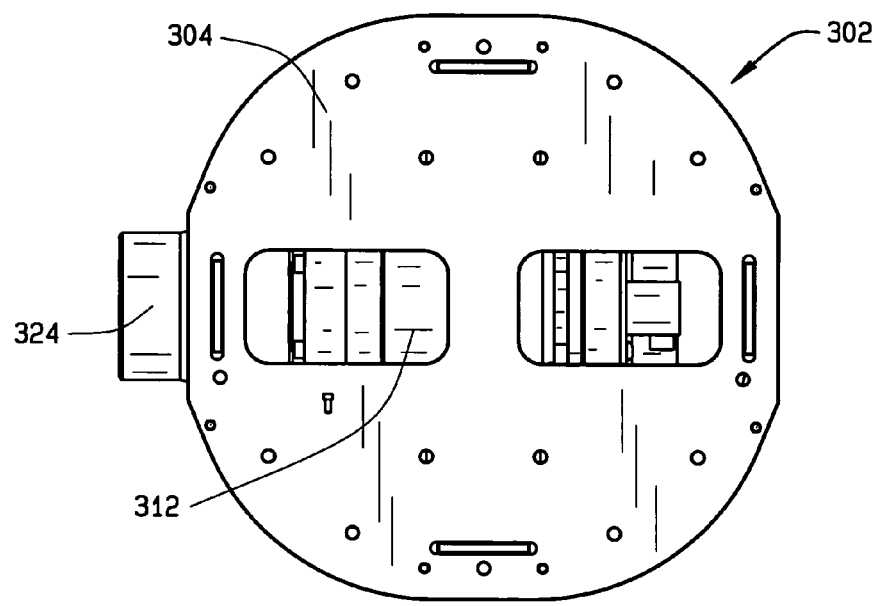
FIG. 15 is a front elevation view of the phi drive mechanism of the magnet assembly.
Figure 16:
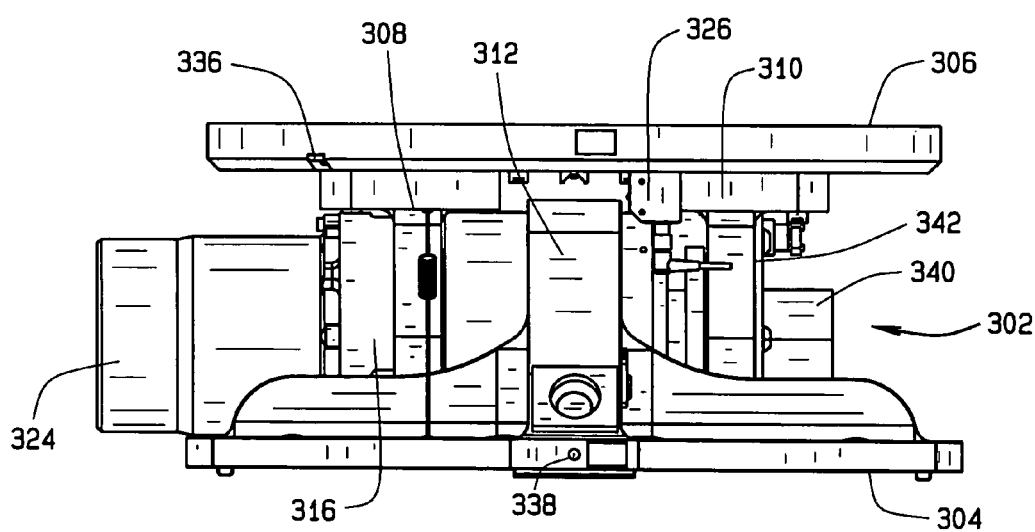
FIG. 16 is a top plan view of the phi drive mechanism.
Figure 17:
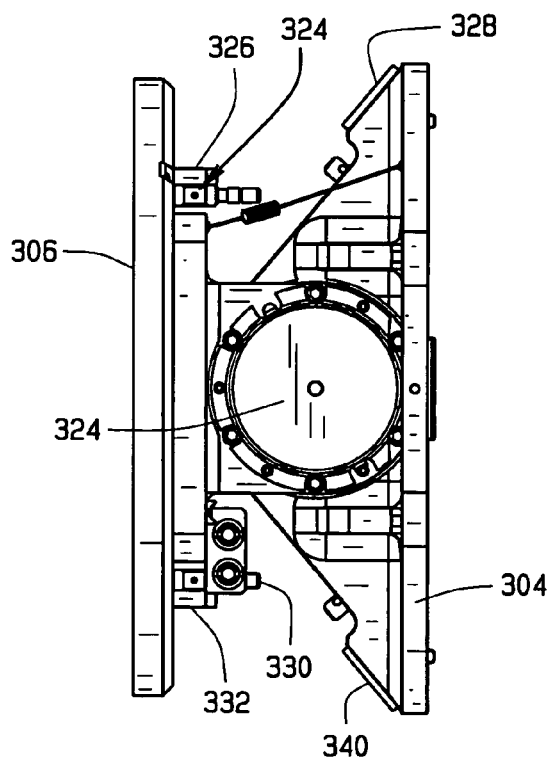
FIG. 17 is a left side elevation view of the phi drive mechanism.
Figure 18:
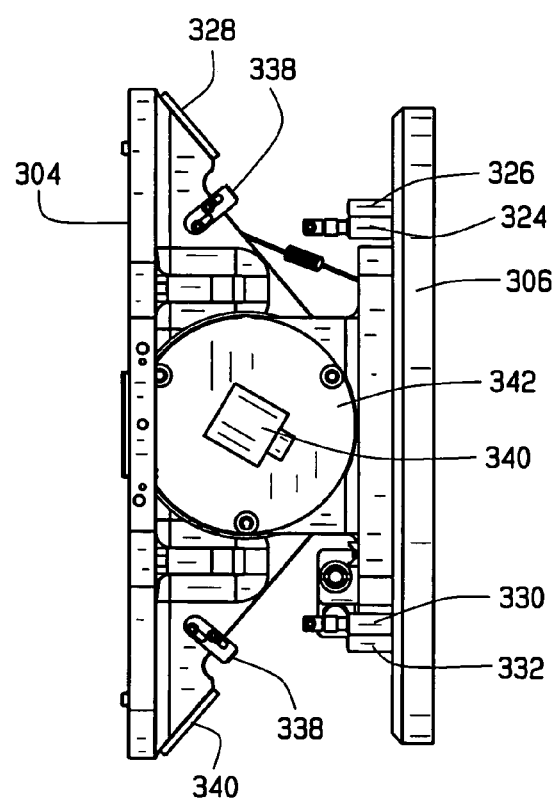
FIG. 18 is a right side elevation view of the phi drive mechanism.

As shown in FIG. 8, the mechanism 300 preferably comprises a φ pivot mechanism 302, for pivoting the magnet 100 in the φ direction; a θ-rotation mechanism 402, for rotating the magnet 100 in the θ-direction; and a z-drive mechanism 602 for translating the magnet in the z-direction.

As shown in FIGS. 15–22, the φ pivot mechanism 302 comprises a front plate 304, adapted for mounting the magnet 100. The front plate 304 is pivotally mounted to a back plate 306. The back plate 306 is adapted to be mounted on the θ-rotation mechanism 402, and has two parallel brackets 308 and 310 projecting from its front face for mounting the front plate 304. A hub 312 on the back of the front plate 304 is pivotally mounted between the brackets 308 and 310, so that the front plate can pivot. In this preferred embodiment, the front plate 304, and thus the magnet 100 mounted on the front plate can pivot plus and minus 40°, for a total range of motion of 80°. This range of motion is based upon the properties of the magnet 100, which in this preferred embodiment provides a 180° change in field direction over a range of pivoting of 80°. With a different magnet, the range of pivoting could be made larger or smaller, as desired.

Figure 23:
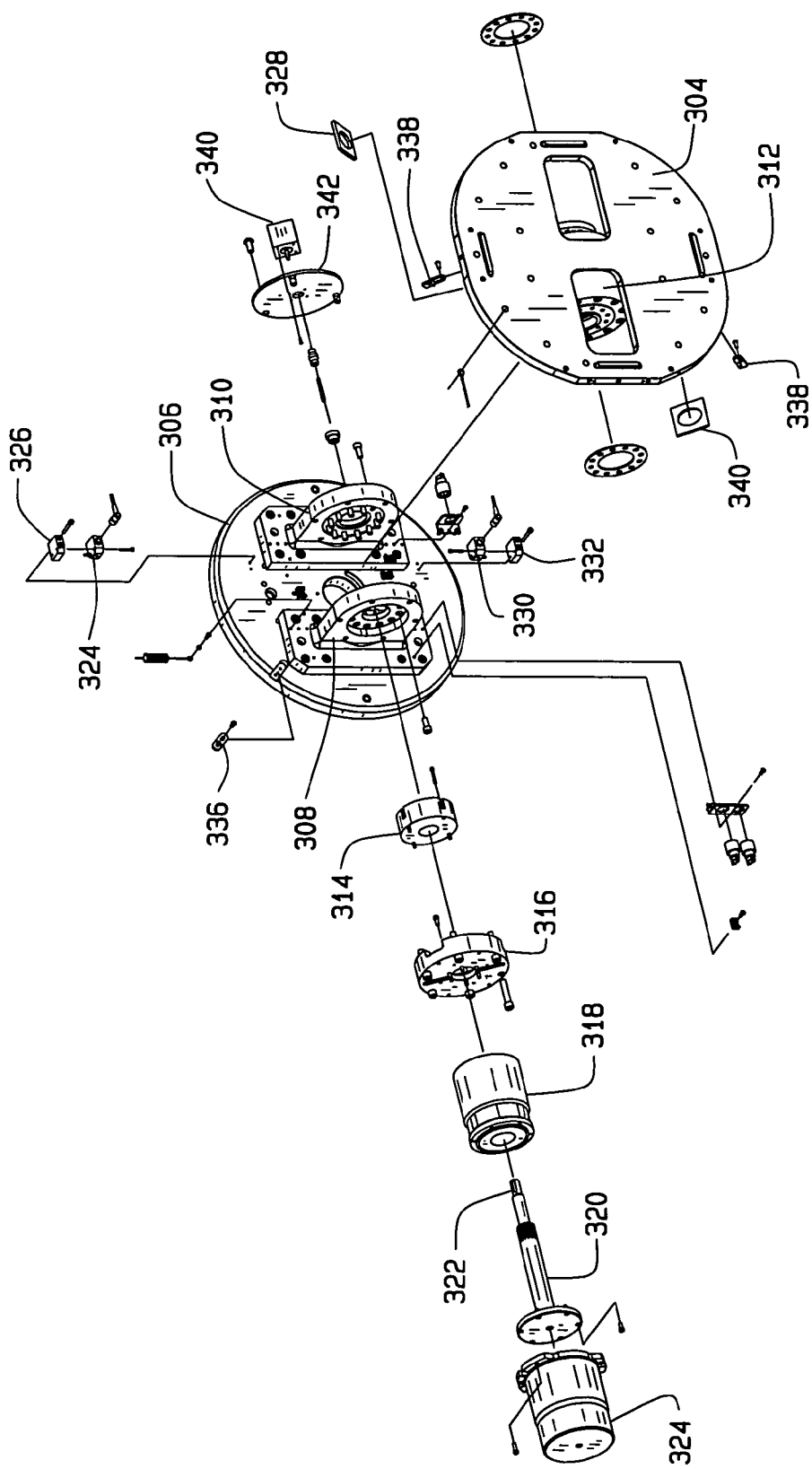
FIG. 23 is an exploded perspective view of the phi drive mechanism.
Figure 24:
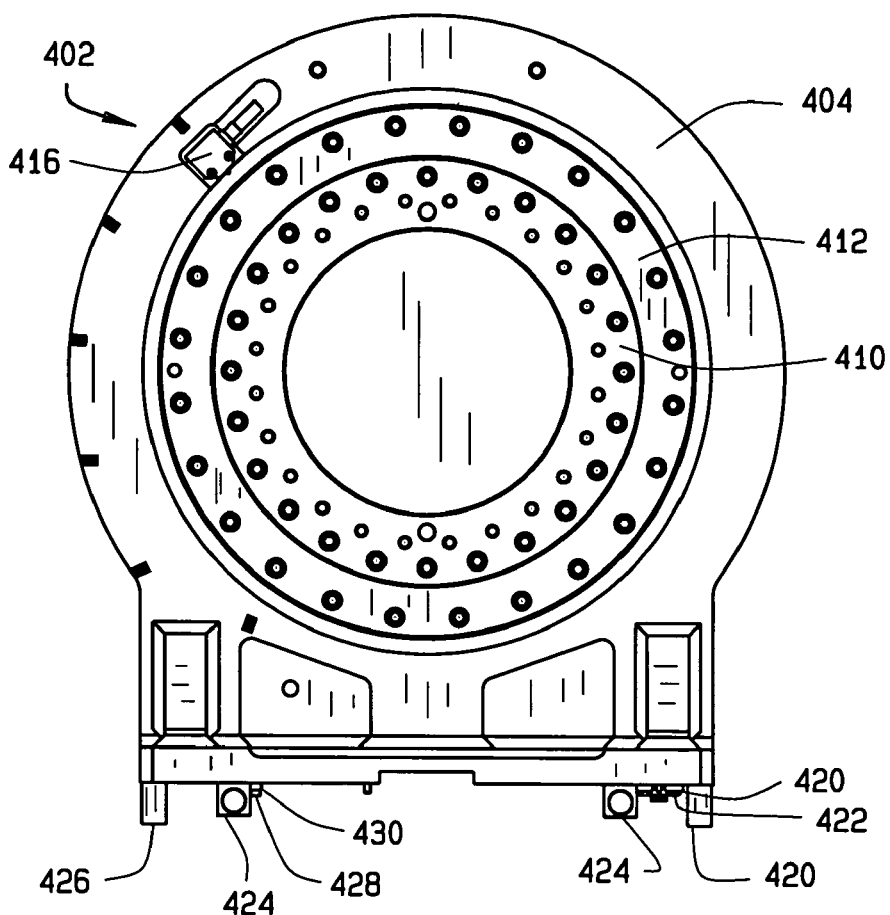
FIG. 24 is a front elevation view of the theta drive mechanism of the magnet assembly.
Figure 25:
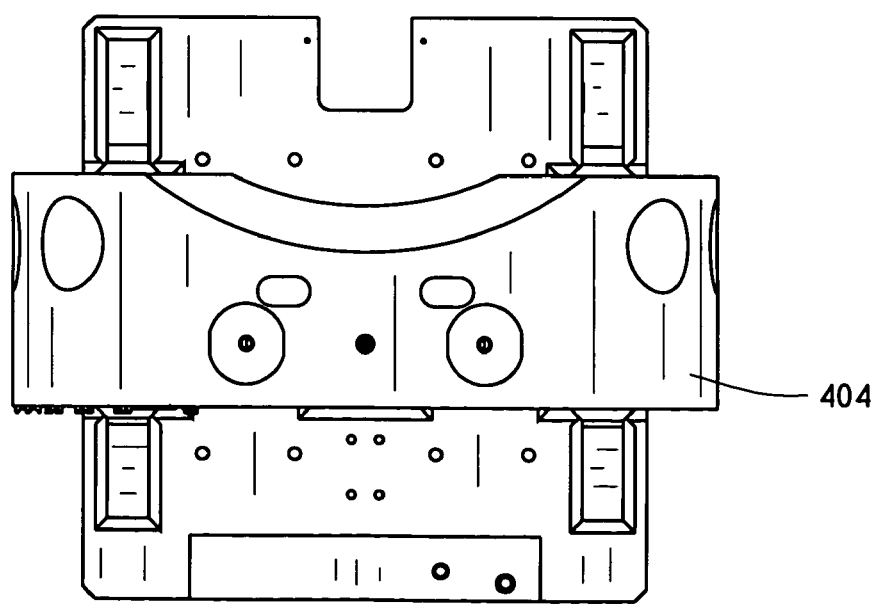
FIG. 25 is a top plan view of the theta drive mechanism.
Figure 26:
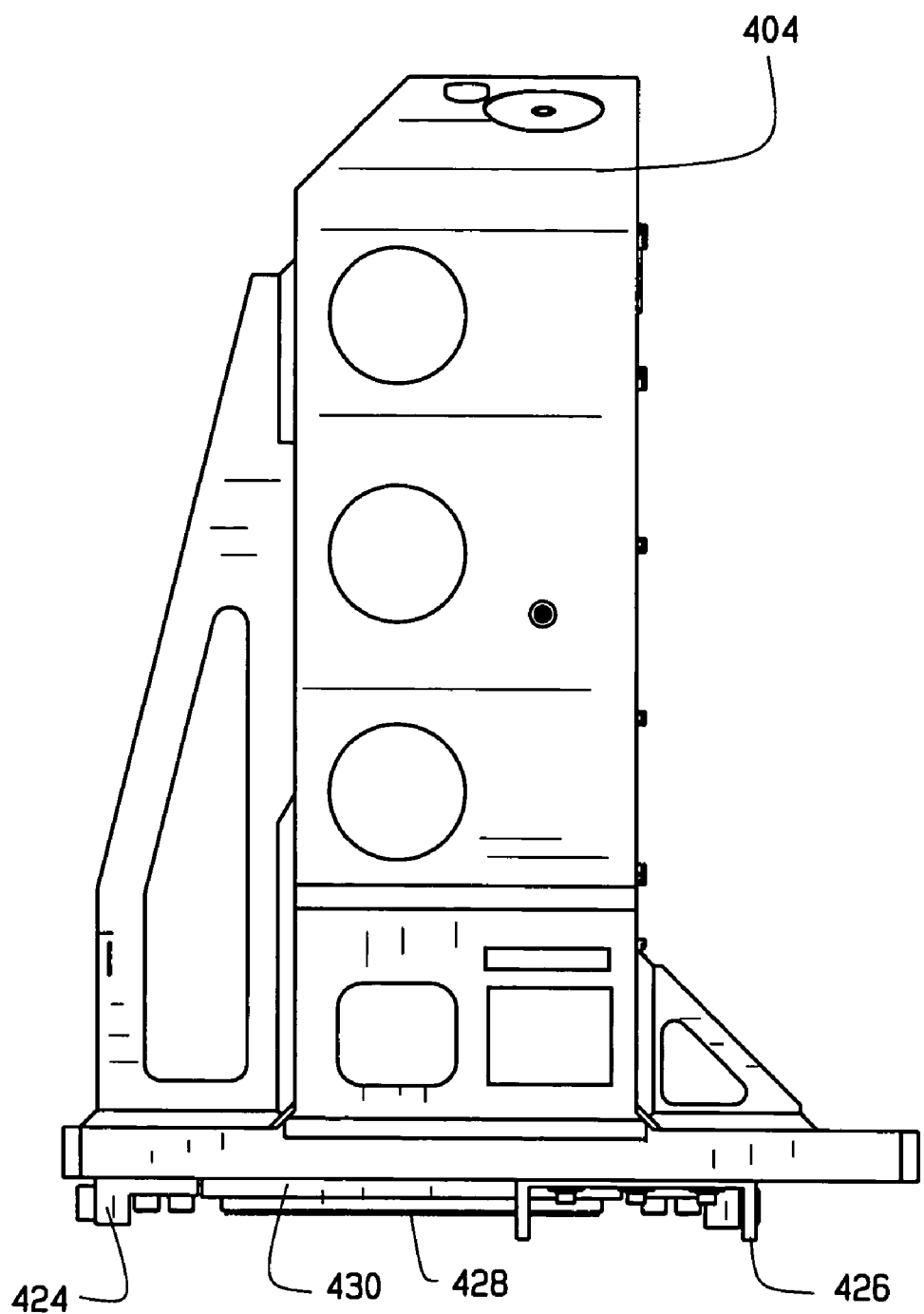
FIG. 26 is a left side elevation view of the theta drive mechanism.
Figure 27:
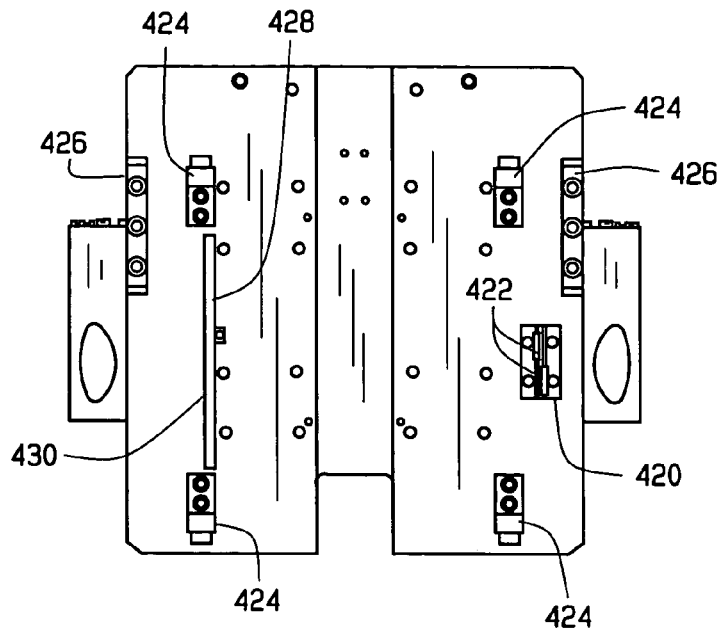
FIG. 27 is a bottom plan view of the theta drive mechanism.

As best shown in FIG. 23, a motor brake 314 is mounted on bracket 308, a motor mounting adapter 316 is mounted over the motor brake on the bracket 308. A motor 318 is mounted on the mounting adapter 316, to turn drive shaft 320 having key 322 thereon. A housing 24 encloses the motor 318. The drive shaft 320 engages the front plate 304 so that rotation of the drive shaft caused by motor 318 causes the plate to pivot about the φ pivot mechanism.

A +φ limit switch 324 is mounted on a block 326 on the front face of plate 306, and is adapted to engage a stop 328 on the front plane 304. Similarly, a −φ limit switch 330 is mounted on a block 332 on the front face of plate 308, and is adapted to engage a stop 334 on the front plate. A theta sensor flag 336, which is used by the theta position sensor as described below, is secured on the back plate 306. Phi sensor flags 338 are secured on the back of front plate 304. A rotary encoder 340 is mounted on an encoder mounting plate 342, on the bracket 310, and is driven by the key 322 on the drive shaft 320.

Figure 28:
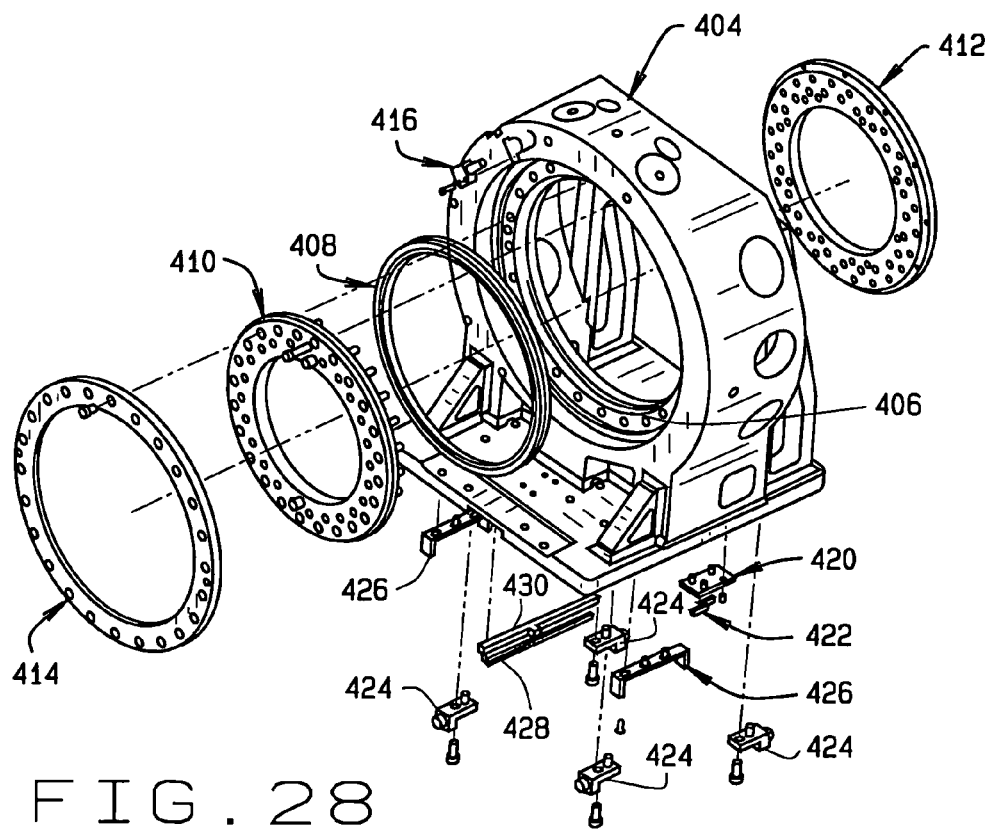
FIG. 28 is a front perspective view of the theta drive mechanism.
Figure 29:
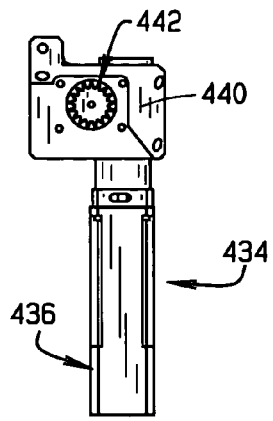
FIG. 29 is a front elevation view of theta drive motor.
Figure 30:
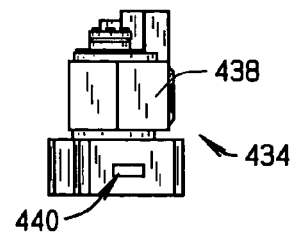
FIG. 30 is a top plan view of the theta drive motor.
Figure 31:
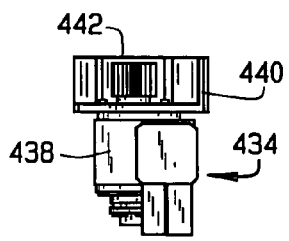
FIG. 31 is a bottom plan view of the theta drive motor.
Figure 32:
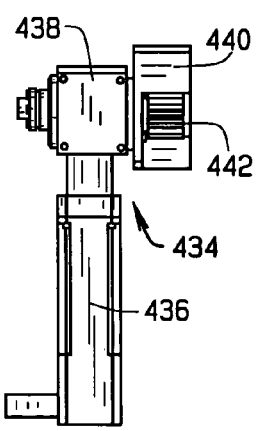
FIG. 32 is a left side elevation view of the theta motor.
Figure 33:
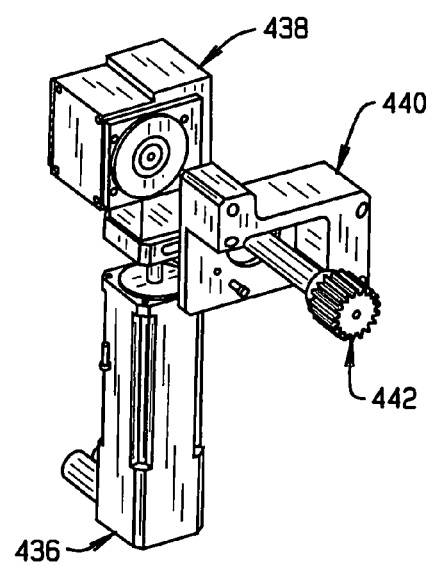
FIG. 33 is an exploded front perspective view of the theta motor.
Figure 34:
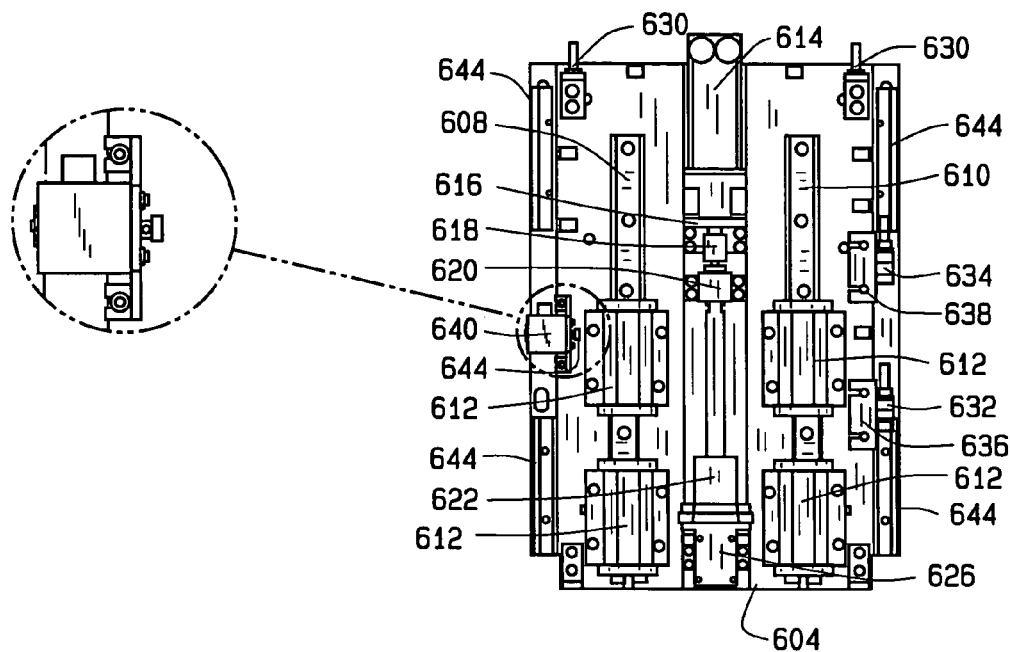
FIG. 34 is an front elevation view of the z drive mechanism.
Figure 35:
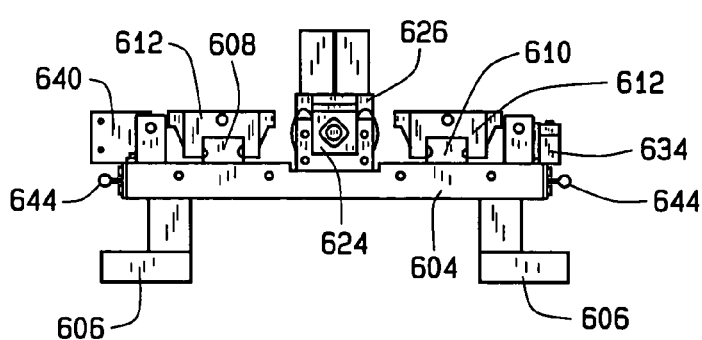
FIG. 35 is a left side elevation view of the z drive mechanism.
Figure 36:
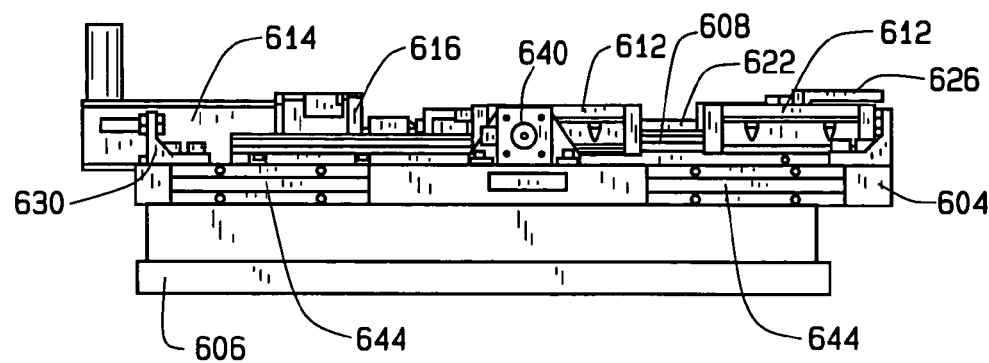
FIG. 36 is a right side elevation view of the z drive mechanism.
Figure 37:
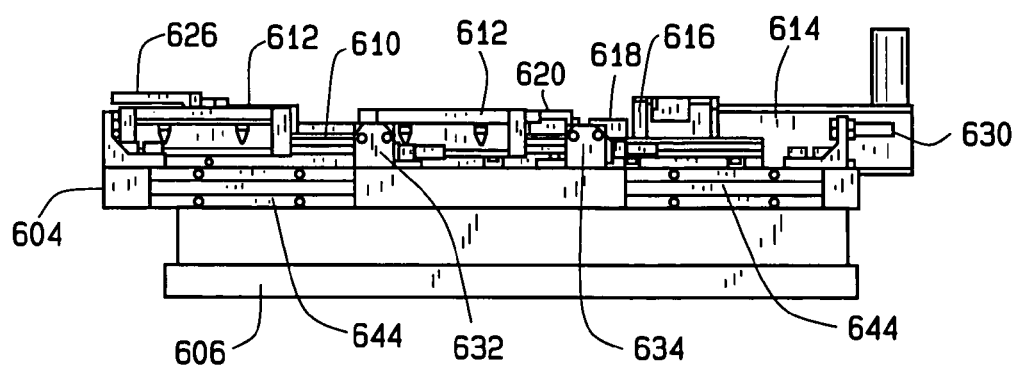
FIG. 37 is bottom plan elevation of the z drive mechanism.
Figure 38:
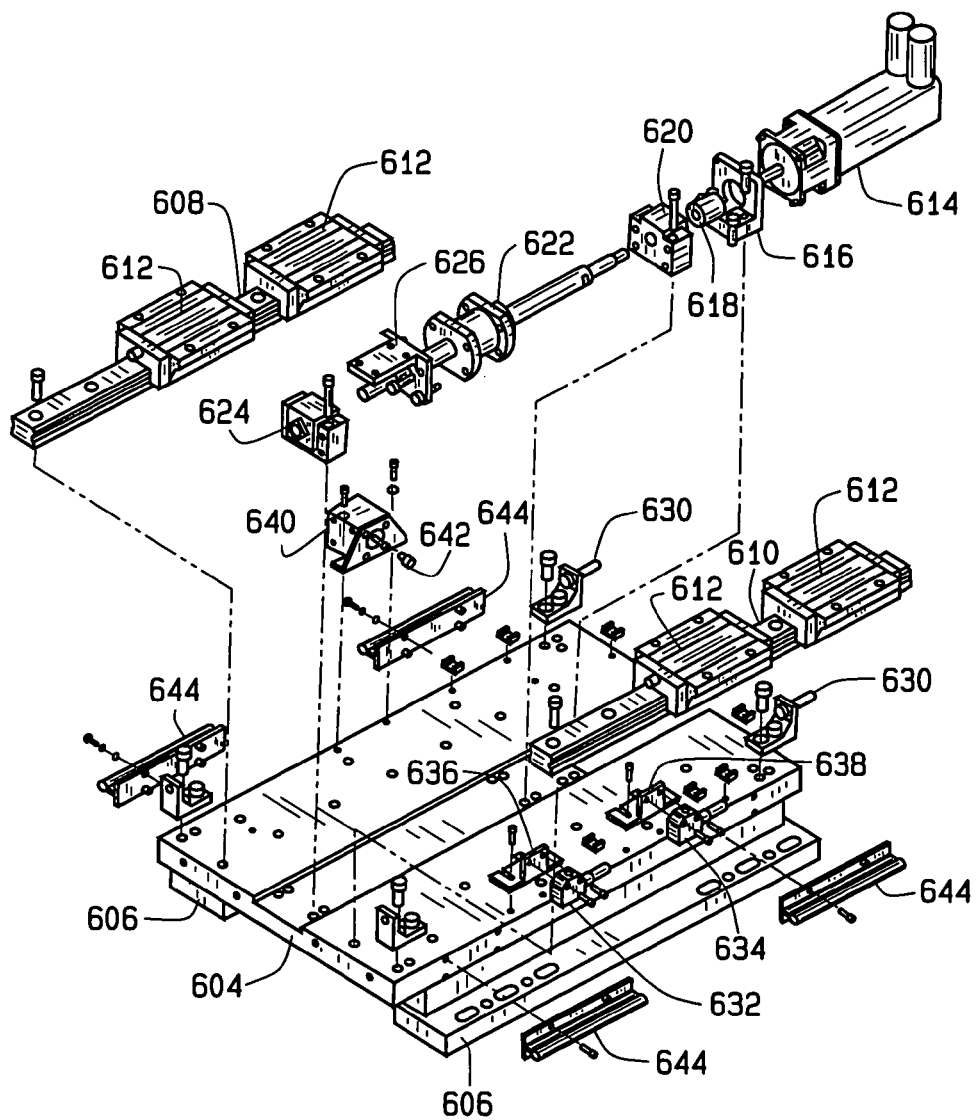
FIG. 38 is an exploded perspective view of the z drive mechanism

The θ rotation mechanism 402 is shown in FIGS. 24–28. The θ rotation mechanism 402 comprises a carriage 404, which is preferably made of aluminum or other strong, lightweight, non-magnetic material. As best shown in FIG. 28, the carriage 404 has a generally cylindrical opening 406 therein in which the outer race of a bearing 408 is mounted. Front and rear retaining hubs 410 and 412 are secured together, sandwiching the inner race of the bearing 408 between them. A retaining ring is mounted in the carriage 404 over the front retaining hub 414. The phi pivot mechanism 302 is mounted to the front retaining hub 410, for rotation around about the theta axis.

A position sensor 416 is mounted in a recess in the front of the carriage 404, and is triggered by the flag 338 on the phi pivot mechanism.

A cam tray 420, mounting a cam 422, is also secured on the bottom of the carriage 404. A plurality of stops 424 are also mounted on the bottom of the carriage 404. A pair of C-shaped brackets 426 are mounted on the bottom of the carriage for engage and moving the cover as the theta mechanism 402 moves in the z direction, as described below. A precision gear 428 is mounted on a bracket 430 on the bottom of the carriage. The precision gear is used in sensing the position in the z-direction as a back up to the position sensing built in to the z drive mechanism 602.

The driver for the θ rotation mechanism 402 is indicated generally as 434 in FIGS. 29–33. The driver 434 comprises a servo motor 436, a gear box 438, a reducer mounting plate 440, and a pinion 442. The pinion 440 engages and drives a gear 442 secured to the rear hub 444, causing rotation in the theta direction.

As shown in FIGS. 35–38, the z drive mechanism 602 comprises base plate 604. Mounting plates 606 are provided on the underside of base plate, on either side, for securing the base plate to the pedestal 800. Tracks 608 and 610 are mounted on the plate 604. Two carriages 612 are slidably mounted on each of the tracks 608 and 610, for slidably mounting the carriage 404 of the theta drive mechanism 402. A servo motor 614 is mounted on the base plate 604 with a bracket 616. A flexible shaft coupling 618, drive screw bearing 620 connect ball screw shaft 622 to the servo motor 614. The end of the ball screw shaft 622 is supported in drive screw bearing 624. A bracket 626 is mounted on the ball screw shaft 622 and is secured to the underside of the carriage 402, to move the carriage.

Stops 628 are mounted on the base plate 604 adjacent one end. Stops 630 are mounted on the base plate 604 adjacent the other end. Limit switches 632 and 634 are mounted on the plate 604 with brackets 636 an 638, respectively. A rotary encoder 640 is mounted on the base plate 604, and has a pinion 642. The pinion 642 engages the precision gear 428 on the bottom of the carriage 404, and measures the position of the carriage relative to the base plate 604. Rails 644 are mounted on the sides of the base plate 604 for slidably mounting the cover 200.

Figure 39:
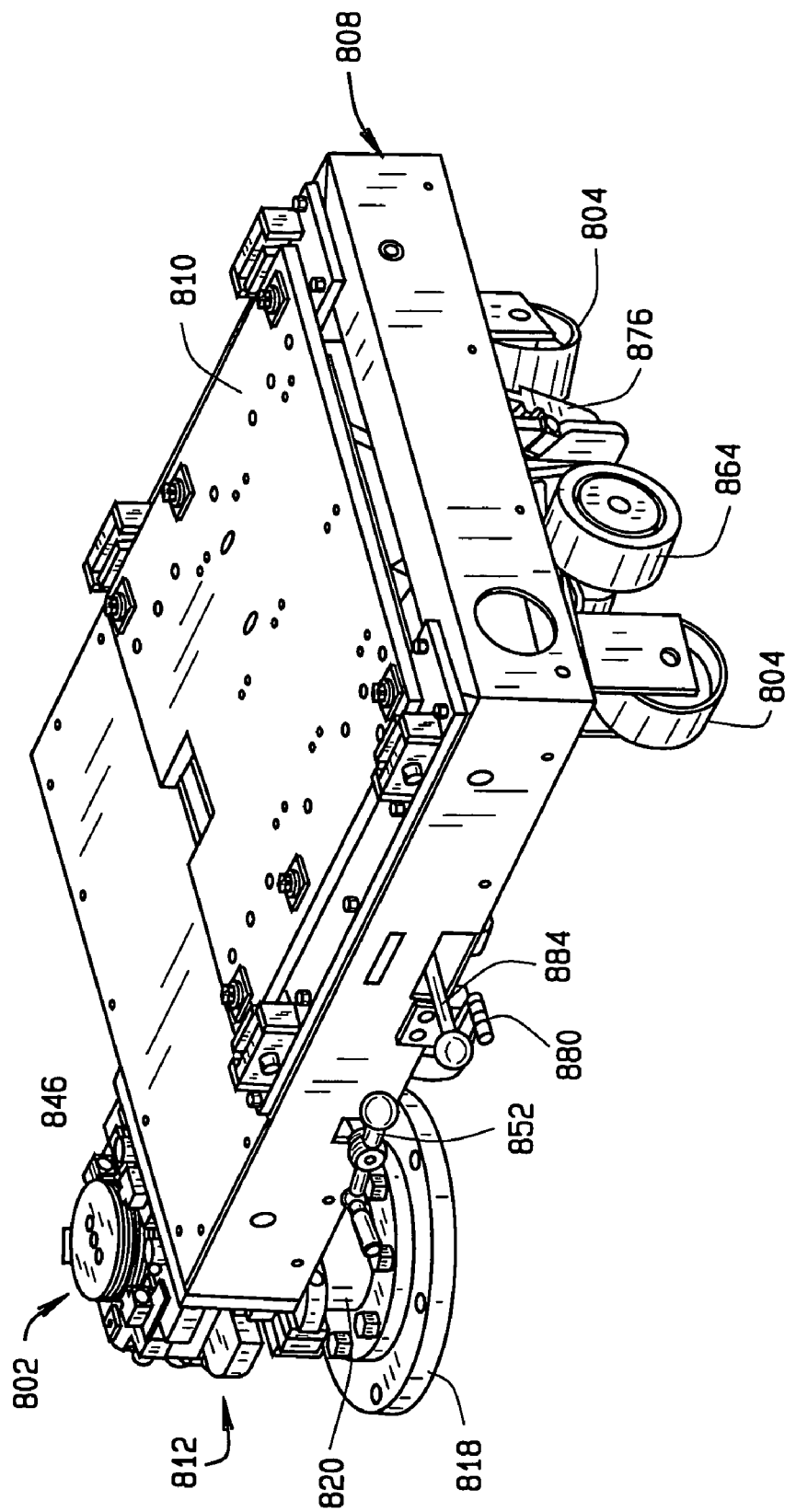
FIG. 39 is a perspective view of the pedestal.

As shown in FIG. 39, the pedestal 800 comprises a frame 808, with a platform 810 for mounting the mechanism 402. The pedestal 800 is pivotally mounted for rotation about post 402, which is secured to the floor of the operating room. A collar 812 secured to the frame 808 surrounds, and rotates around the post 402. A drive mechanism 814 is mounted in the frame 808, for driving the pedestal 800 to rotate around the post 402. A lock mechanism 816 is also mounted in the frame 808, for securing the pedestal against movement.

Figure 40:
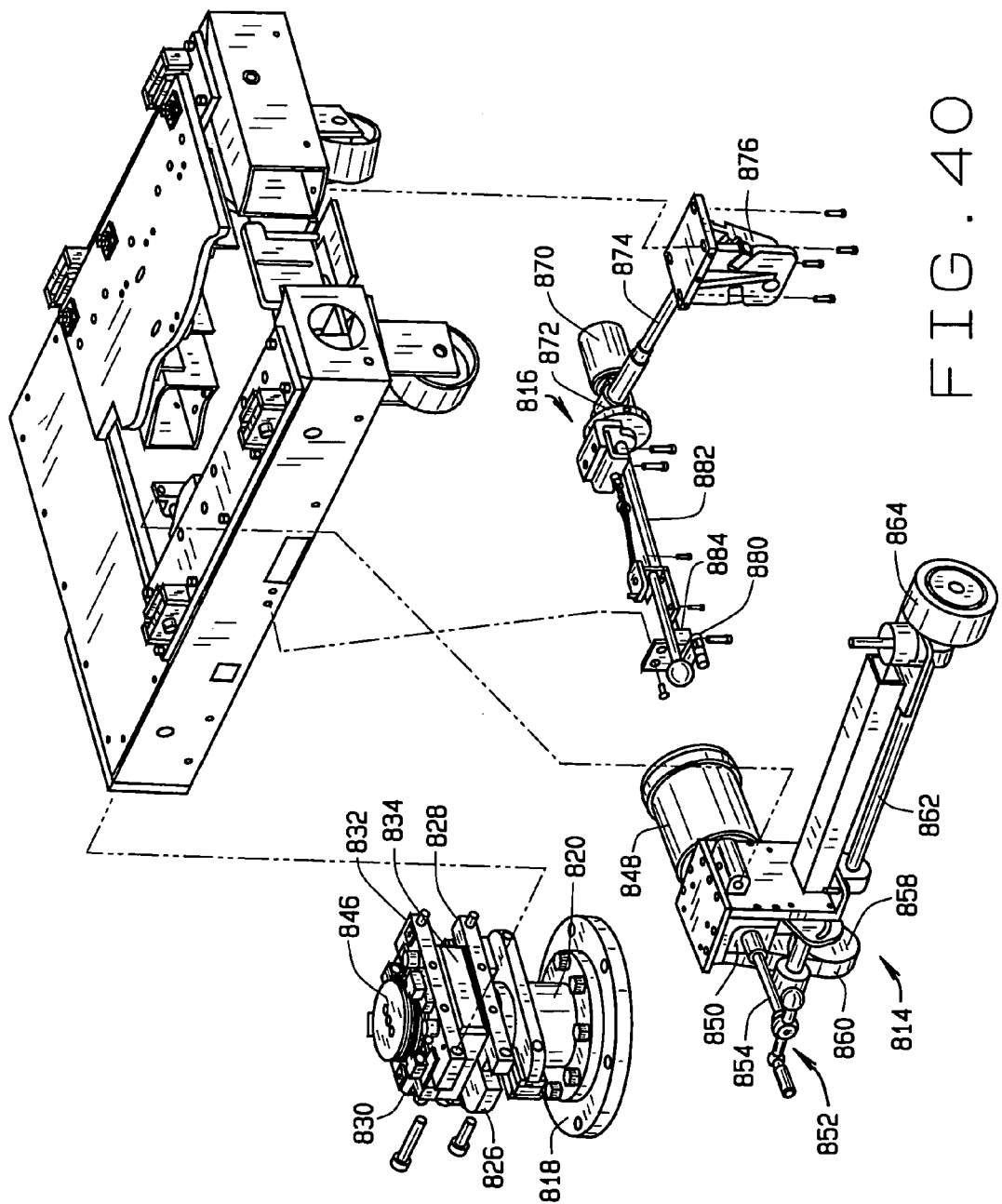
FIG. 40 is an exploded front perspective view of the pedestal showing the pivot assembly, the drive system assembly, and the locking system.
Figure 41:
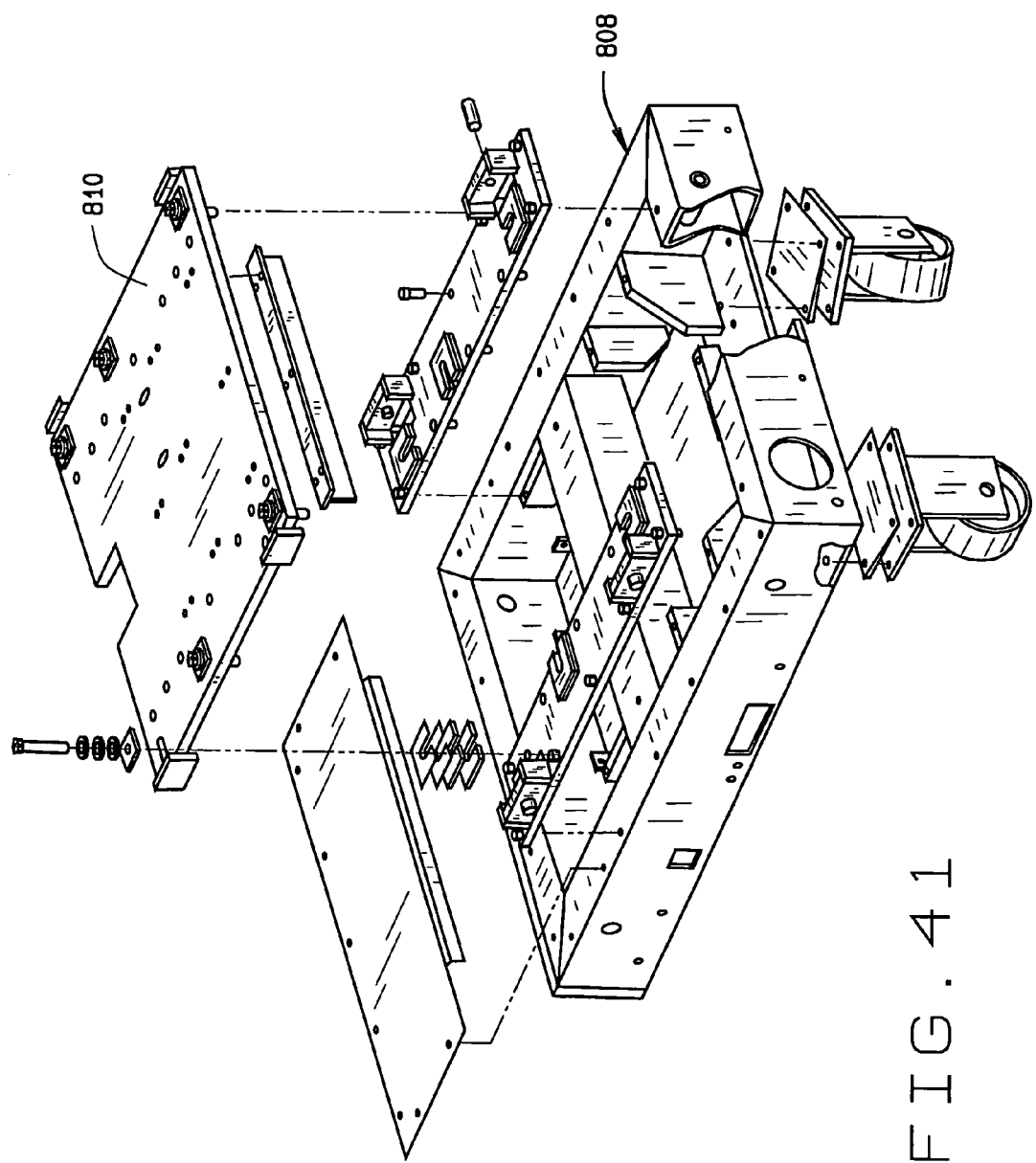
FIG. 41 is an exploded front perspective view of the pedestal with the pivot assembly, the drive system assembly, and the locking system assembly removed.
Figure 42:
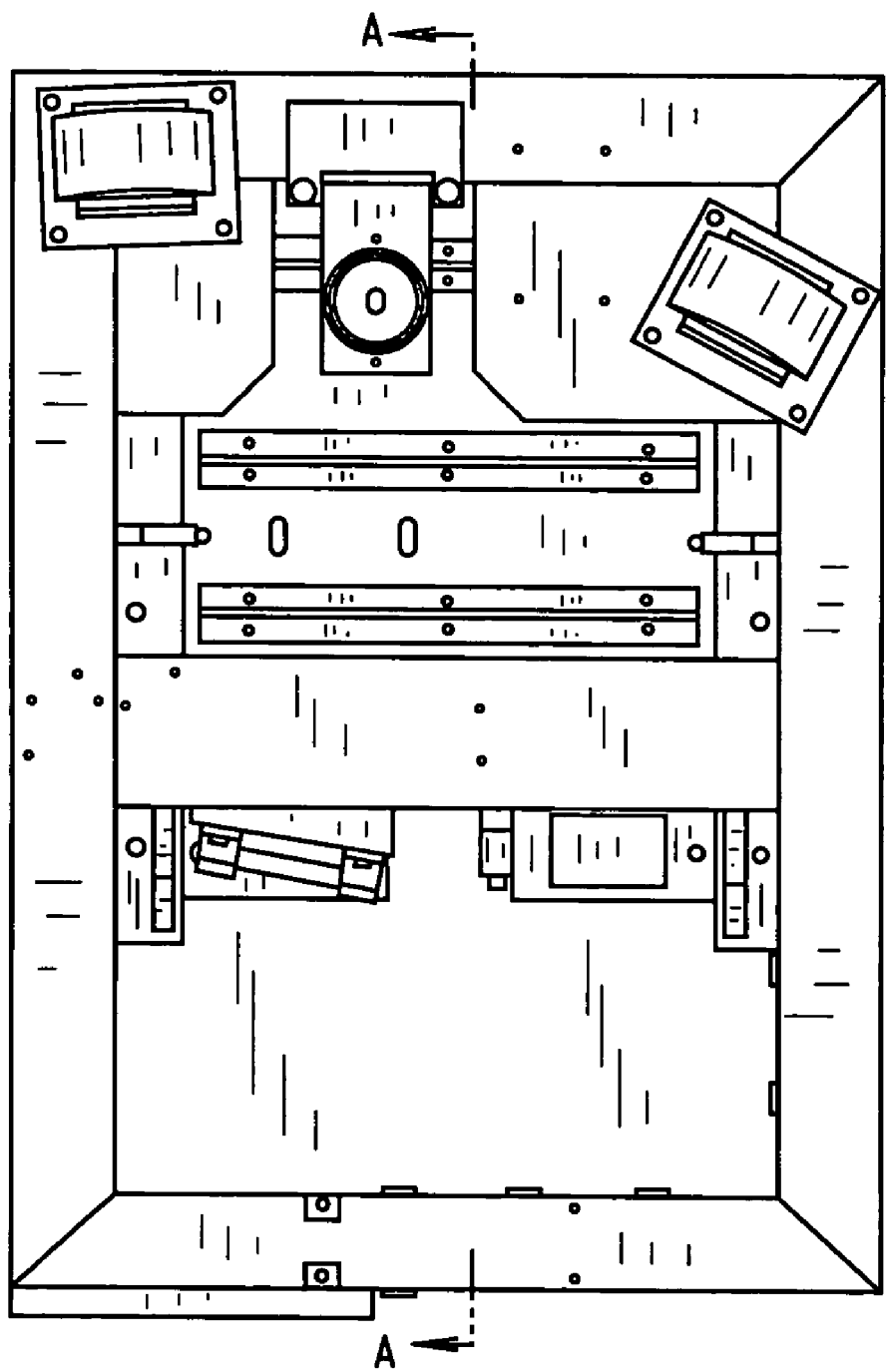
FIG. 42 is a bottom plan view of the pedestal.
Figure 43:
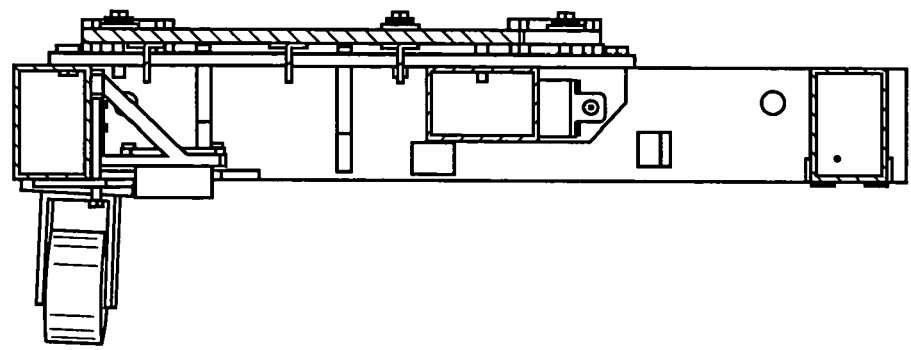
FIG. 43 is a longitudinal cross sectional view of the pedestal taken along the plane of line 43—43 in FIG. 42.
Figure 44:
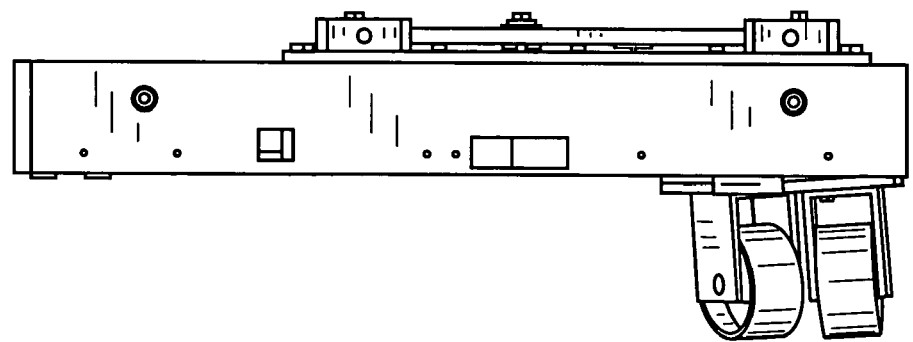
FIG. 44 is a side elevation view of the pedestal.
Figure 45:
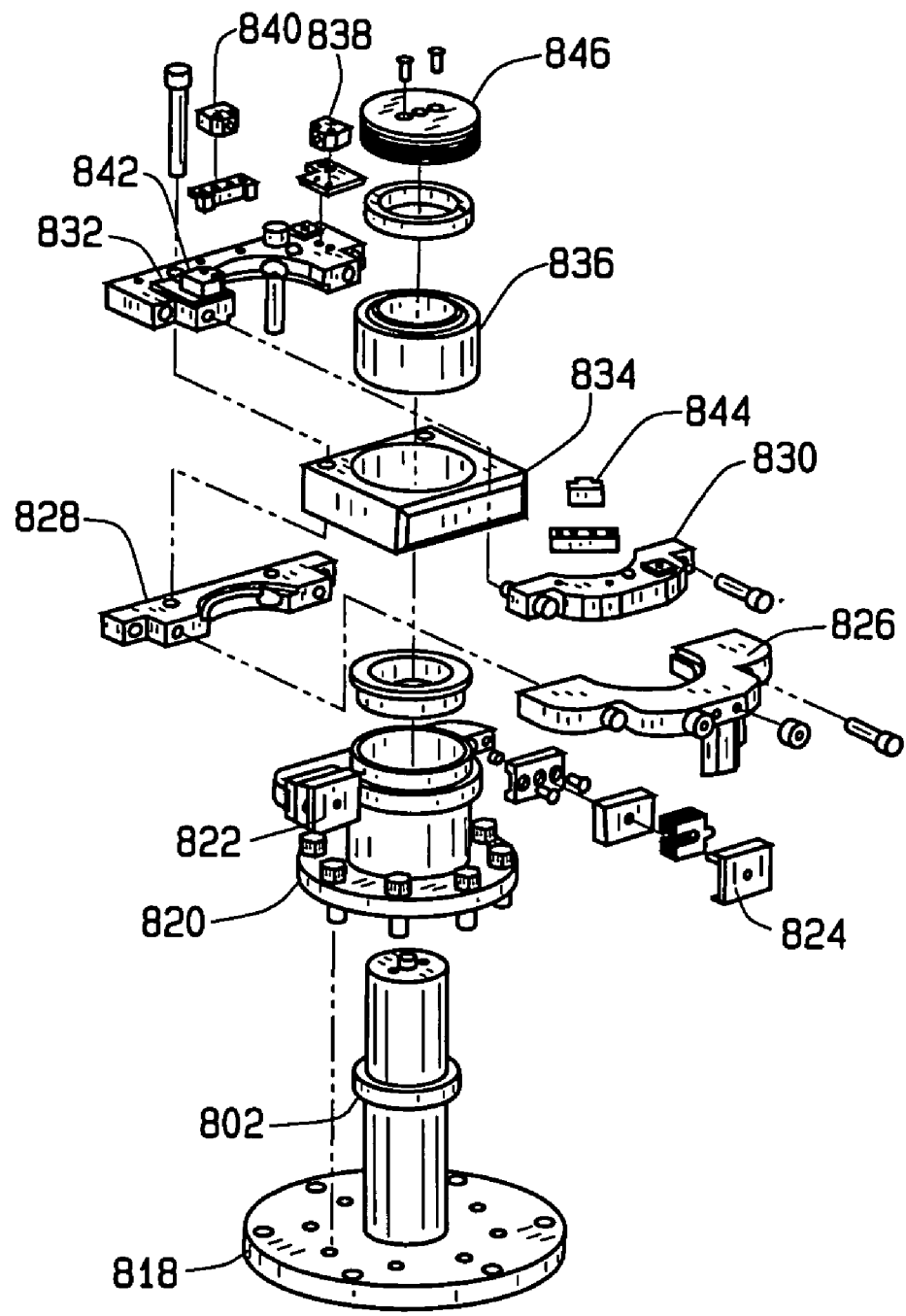
FIG. 45 is an exploded perspective view of the pivot assembly for pivotally mounting the pedestal.

As shown in FIGS. 40 and 45, the post 802 is surrounded by a weldment 818. A stop tube 820 is mounted over the post 802, providing stops 822 and 824 for limiting the rotational movement of the pedestal. Lower outer mounting plate 826 and lower inner mounting plate 828, and upper outer mounting plate 830 and upper inner mounting 832 are secured above and below block 834, mounting spherical bearing 836. Limit switches 838, 840, 842, and 844 are mounted on the upper mounting ring and are tripped by movement relative to cam 846 secured on the top of the post 802.

Figure 46:
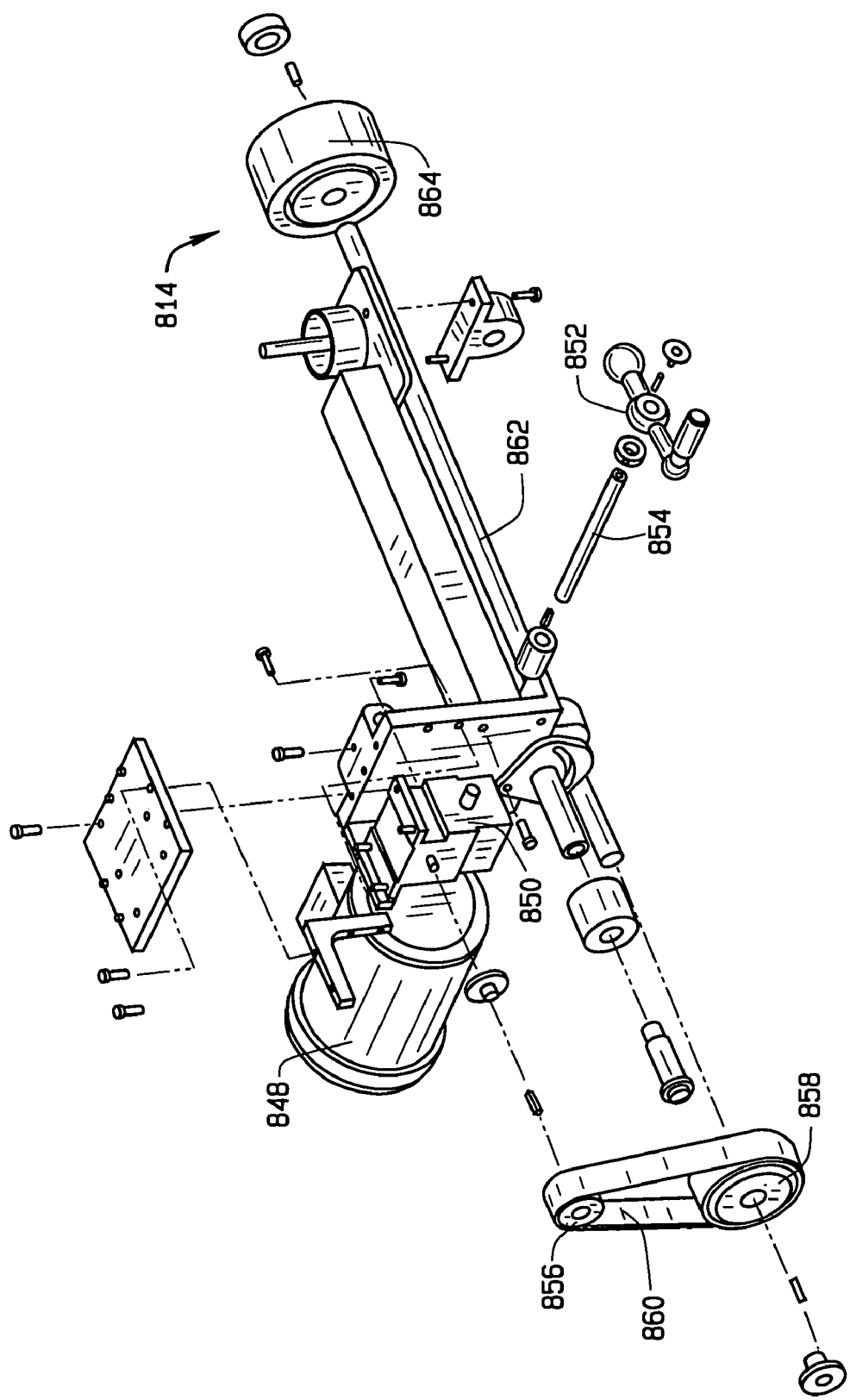
FIG. 46 is a perspective view of the drive mechanism.

As shown in FIGS. 40 and 46, the drive mechanism 814 comprises a motor 848 connected to gear box 850. A hand crank 852 on shaft 854 is also connected to gear box 850. Sheaves 856 and 858 and belt 860 connect the gear box 850 to the drives shaft 862, which in turn drives drive wheel 864. Thus the motor can operate the drive wheel, or in a situation where power is not available, hand crank 852 an be used to operate the drive wheel, and pivot the pedestal around post 802.

Figure 47:
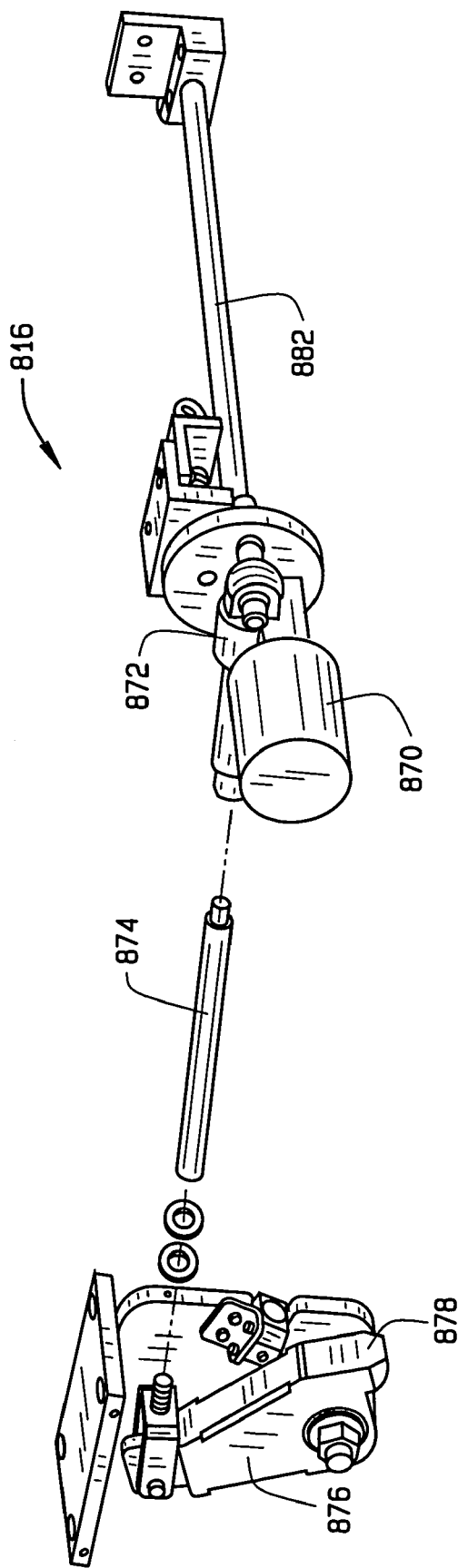
FIG. 47 is a perspective view of the drive assembly.
Figure 48:
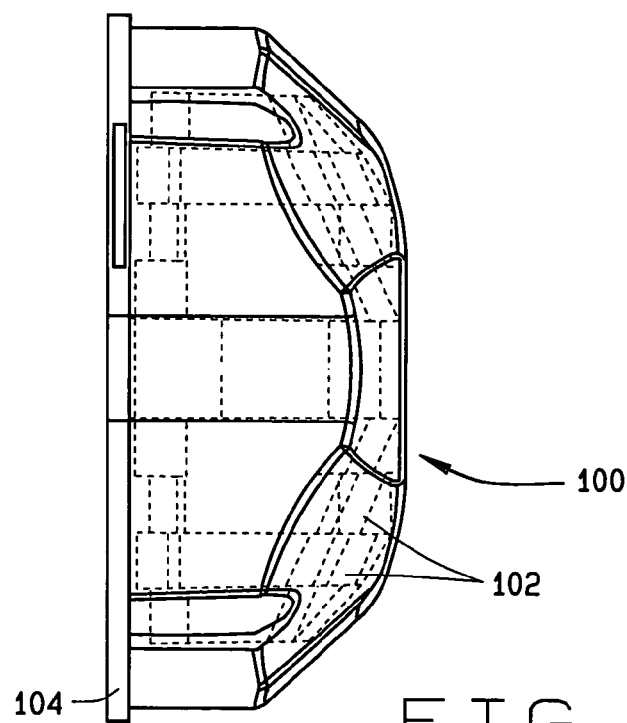
FIG. 48 is a side elevation view of the magnet.
Figure 49:
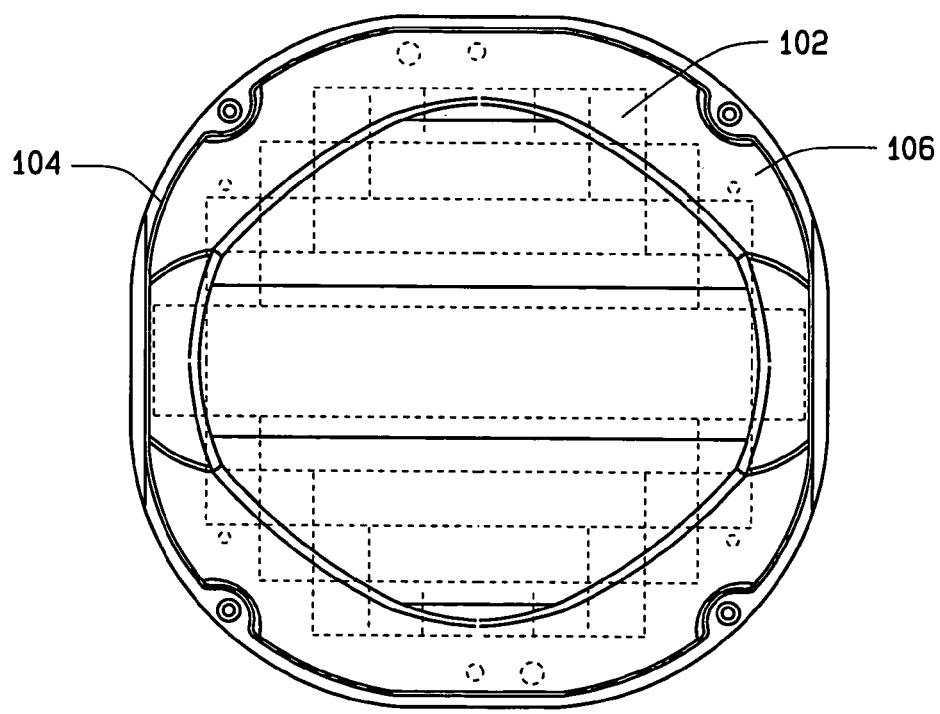
FIG. 49 is a front elevation view of the magnet.

As shown in FIGS. 40 and 47, the lock mechanism 816 comprises an electric motor 870 which turns a gear box 872 to pull or push rod 874. The pulling or pushing of the rod 874 causes the lock member 876 to pivot. The lock member 876 has a tab 878, which pivots into and engages a slot in the floor of the procedure room. A hand crank 880 on shaft 882 also turns the gear box 872, to manually pull or push rod 874. An spring biased interlock bar 884, interferes with the hand crank, and must be manipulated out of the way in order to manually operate the lock mechanism 816.

What is claimed is:

1. A magnet system for applying a magnetic field of selected direction to an operating region inside a patient on a support, to control a magnetic medical object in the operating region, the magnet system comprising first and second magnet applicators on opposite sides of the patient support, each magnet applicator comprising a base, and a magnet mounted on the base, each base being movable to change the position and/or orientation of the magnet relative to the operating position, to move the magnet from a state in which magnet applies a field to the operating region, and a second position in which the magnet does not apply a field to the operating region.

2. The system according to claim 1 wherein the bases pivot to change the orientation of the magnet relative to the patient.

3. The system according to claim 1 wherein the bases pivot to change the position and orientation of the magnet relative to the patient.

* * * * *